(12) United States Patent
Binkowski et al.

(10) Patent No.: US 9,738,921 B2
(45) Date of Patent: Aug. 22, 2017

(54) COMPOSITIONS AND METHODS FOR MONITORING TRANSMEMBRANE TRAFFICKING

(71) Applicant: Promega Corporation, Madison, WI (US)

(72) Inventors: Brock F. Binkowski, Sauk City, WI (US); Mei Cong, Madison, WI (US); Matthew B. Robers, Madison, WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 14/800,352

(22) Filed: Jul. 15, 2015

(65) Prior Publication Data

US 2015/0322482 A1 Nov. 12, 2015

Related U.S. Application Data

(62) Division of application No. 13/683,662, filed on Nov. 21, 2012, now Pat. No. 9,096,889.

(60) Provisional application No. 61/563,294, filed on Nov. 23, 2011.

(51) Int. Cl.
| | | |
|---|---|---|
| *C12Q 1/66* | (2006.01) | |
| *G01N 33/567* | (2006.01) | |
| *G01N 33/50* | (2006.01) | |
| *G01N 33/58* | (2006.01) | |

(52) U.S. Cl.
CPC ............ *C12Q 1/66* (2013.01); *G01N 33/5005* (2013.01); *G01N 33/567* (2013.01); *G01N 33/58* (2013.01)

(58) Field of Classification Search
None
See application file for complete search history.

(56) References Cited

U.S. PATENT DOCUMENTS

| | | | | |
|---|---|---|---|---|
| 7,455,982 | B2 * | 11/2008 | Barak | ............... C12N 15/1089 435/325 |
| 2002/0102687 | A1 | 8/2002 | Inouye | |
| 2004/0029190 | A1 | 2/2004 | Barak et al. | |
| 2004/0101912 | A1 | 5/2004 | Rubin et al. | |
| 2008/0233558 | A1 | 9/2008 | Merten | |
| 2013/0196357 | A1 | 8/2013 | Binkowski et al. | |

FOREIGN PATENT DOCUMENTS

| | | |
|---|---|---|
| JP | H08-098680 | 4/1996 |
| JP | 2007-330252 | 12/2007 |
| WO | 00/49416 | 8/2000 |
| WO | 2010/012962 | 4/2010 |
| WO | 2011/067202 | 6/2011 |

OTHER PUBLICATIONS

Wehrman et al., Nature Methods, 2006, vol. 3, No. 4, p. 295-301.*
Blot et al., Use of Quantitative Immunofluorescence Microscopy to Study Intracellular Trafficking, Methods in Molecular Biology, 2008, 457:347-366.
McLean et al., Visualizing differences in ligand regulation of wild-type and constitutively active mutant beta(2)-adrenoceptor-green fluorescent protein fusion proteins, Mol Pharmocol, 1999, 56:1182-1191.
European Supplementary Search Report for EP Patent Application 12851936.0, received May 20, 2015, 7 pages.
International Search Report and Written Opinion for PCT/US2012/066325, mailed Feb. 19, 2013, 12 pages.
Dictionary of Biology, definition of Endosome, publisher Minako Ozawa, 1st edition, 2010, p. 161, original in Japanese. English translation provided.

* cited by examiner

*Primary Examiner* — Kade Ariani
(74) *Attorney, Agent, or Firm* — Casimir Jones SC; David W. Staple

(57) ABSTRACT

Provided herein are compositions and methods for monitoring the movement of analytes and/or cellular components across biological membranes (e.g., cell surface internalization). In particular, reporter constructs are provided, the transmembrane movement of which (e.g., by endocytosis) is monitored by methods described herein.

10 Claims, 15 Drawing Sheets

Alternate Endpoint Assay Configuration
IL6-OgLuc(9B8)-V2R Internalization
20uM 3939 added after stimulation
50pg/well 30 min stim Alternate Endpoint Assay Configuration
IL6-OgLuc(9B8)-B2AR Internalization
20 uM3939 added after stimulation
50 pg/well, 30 min

PBI 4525

PBI 4377-01

D-Luciferin

PBI 3102

PBI 3939

SEQUENCE LISTING

<160> NUMBER OF SEQ ID NOS: 12

<210> SEQ ID NO 1
<211> LENGTH: 87
<212> TYPE: DNA
<213> ORGANISM: Artificial Sequence

```
<220> FEATURE:
<223> OTHER INFORMATION: Synthetic

<400> SEQUENCE: 1
atgaactcct tctccacaag cgccttcggt ccagttgcct tctccctggg gctgctcctg    60
gtgttgcctg ctgccttccc tgcccca                                        87

<210> SEQ ID NO 2
<211> LENGTH: 12
<212> TYPE: DNA
<213> ORGANISM: Artificial Sequence
<220> FEATURE:
<223> OTHER INFORMATION: Synthetic

<400> SEQUENCE: 2
ggctcgagcg ga                                                        12

<210> SEQ ID NO 3
<211> LENGTH: 513
<212> TYPE: DNA
<213> ORGANISM: Artificial Sequence
<220> FEATURE:
<223> OTHER INFORMATION: Synthetic

<400> SEQUENCE: 3
atggtgttta cactcgaaga tttcgtaggg gactggcggc agacagccgg ctacaacctg    60
gaccaagtcc ttgagcaggg cggtgtgtcc agtttgtttc agaatctcgg ggtgtccgta   120
actccgatcc aaaggattgt cctgagcggt gaaaacggcc tgaagatcga catccatgtc   180
atcatcccgt atgaaggtct gagcggcgat cagatgggcc agatcgaaaa aatttttaag   240
gtggtgtacc ctgtggatga tcatcacttt aaggtgattc tgcactatgg cacactggta   300
atcgacgggg ttacgccgaa catgatcgac tatttcggac ggccgtatga aggcatcgcc   360
gtgttcgacg gcaaaaagat cactgtaacc gggaccctgt ggaacggcaa caaaattatc   420
gacgagcgcc tgatcaaccc cgacggctcc ctgctgttcc gcgtaaccat caacggagtg   480
accggctggc ggctgtgcga gcgcattttg gcg                                513

<210> SEQ ID NO 4
<211> LENGTH: 1629
<212> TYPE: DNA
<213> ORGANISM: Artificial Sequence
<220> FEATURE:
<223> OTHER INFORMATION: Synthetic

<400> SEQUENCE: 4
gctgacaaaa acatcctgta tggtccggaa ccgttctacc cactggaaga tggtaccgct    60
ggtgaacaga tgtttgacgc attatctcgt tatgcagcta ttccgggctg catagcattg   120
acaaatgctc atacaaaaga aaatgtttta tatgaagagt ttctgaaact gtcgtgtcgt   180
ttagcggaaa gttttaaaaa gtatggatta aacaaaacg acacaatagc ggtgtgtagc   240
gaaaatagtc tgcaatttt ccttcctgta attgcatcat tgtatcttgg aataattgtg   300
gcacctgtta acgataaata cattgaacgt gaattaatac acagtcttgg tattgtaaaa   360
ccacgcatag ttttttgctc caagaatact tttcaaaaag tactgaatgt aaaatctaaa   420
ttaaaatcta ttgaaactat tattatatta gacttaaatg aagacttagg aggttatcaa   480
tgcctcaaca actttatttc tcaaaattcc gatagtaatc tggacgtaaa aaaatttaaa   540
ccctattctt ttaatcgaga cgatcaggtt gcgtcgatta tgttttcttc tggtacaact   600
```

```
ggtctgccga agggagtcat gctaactcac aagaatattg ttgcacgatt ttctattgca      660
aaagatccta cttttggtaa cgcaattaat cccacgtcag caattttaac ggtaataacct     720 ttccaccatg gttttggtat gatgaccaca ttaggatact ttacttgtgg attccgagtt     780
gttctaatgc acacgtttga agaaaaacta tttctacaat cattacaaga ttataaagtg     840
gaaagtactt tacttgtacc aacattaatg gcatttcttg caaaaagtgc attagttgaa     900
aagtacgatt tatcgcactt aaaagaaatt gcatctggtg gcgcaccttt atcaaaagaa     960
attggggaga tggtgaaaaa acggtttaaa ttaaactttg tcaggcaagg gtatggatta    1020
acagaaacca cttcggctgt tttaattaca ccgaaaggtg acgccaaacc gggatcaact    1080
ggtaaaatag taccattaca cgctgttaaa gttgtcgatc ctacaacagg aaaaattttg    1140
gggccaaatg aacctggaga attgtatttt aaaggcccga tgataatgaa gggttattat    1200
aataatgaag aagctactaa agcaattatt gataatgacg gatggttgcg ctctggtgat    1260
attgcttatt atgacaatga tggccatttt tatattgtgg acaggctgaa gtcactgatt    1320 aaaatataaag gttatcaggt tgcacctgct gaaattgagg gaatactctt acaacatccg    1380
tatattgttg atgccggcgt tactggtata ccggatgaag ccgcgggcga gcttccagct    1440
gcaggtgttg tagtacagac tggaaaatat ctaaacgaac aaatcgtaca agattatgtt    1500
gccagtcaag tttcaacagc caaatggcta cgtggtgggg tgaaattttt ggatgaaatt    1560
cccaaaggat caactggaaa aattgacaga aaagtgttaa gacaaatgtt agaaaaacac    1620
accaatggg                                                          1629

<210> SEQ ID NO 5
<211> LENGTH: 1080
<212> TYPE: DNA
<213> ORGANISM: Homo sapiens

<400> SEQUENCE: 5
atgattctca actcttctac tgaagatggt attaaaagaa tccaagatga ttgtcccaaa      60
gctggaaggc ataattacat atttgtcatg attcctactt tatacagtat catctttgtg     120
gtgggaatat ttggaaacag cttggtggtg atagtcattt actttatat gaagctgaag     180 actgtggcca gtgttttttct tttgaattta gcactggctg acttatgctt tttactgact     240
ttgccactat gggctgtcta cacagctatg gaataccgct ggcccttttgg caattaccta     300 tgtaagattg cttcagccag cgtcagtttc aacctgtacg ctagtgtgtt tctactcacg     360
tgtctcagca ttgatcgata cctggctatt gttcacccaa tgaagtcccg ccttcgacgc     420
acaatgcttg tagccaaagt cacctgcatc atcatttggc tgctggcagg cttggccagt     480
ttgccagcta taatccatcg aaatgtattt ttcattgaga acaccaatat tacagtttgt     540
gctttccatt atgagtccca aaattcaacc cttccgatag ggctgggcct gaccaaaaat     600
atactgggtt tcctgttttcc ttttctgatc attcttacaa gttatactct tatttggaag     660
gccctaaaga aggcttatga aattcagaag aacaaaccaa gaaatgatga tattttttaag     720 ataattatgg caattgtgct tttctttttc ttttcctgga ttccccacca aatattcact     780
tttctggatg tattgattca actaggcatc atacgtgact gtagaattgc agatattgtg     840
gacacggcca tgcctatcac catttgtata gcttattttta acaattgcct gaatcctctt     900
ttttatggct ttctggggaa aaatttaaa agatattttc tccagcttct aaaatatatt     960
ccccaaaaag ccaaatccca ctcaaacctt tcaacaaaaa tgagcacgct ttcctaccgc    1020
ccctcagata atgtaagctc atccaccaag aagcctgcac catgttttga ggttgagtga    1080
```

<210> SEQ ID NO 6
<211> LENGTH: 1119
<212> TYPE: DNA
<213> ORGANISM: Homo sapiens

<400> SEQUENCE: 6

```
atggaaccgg cccccteegc eggegeegag etgcageeee egetetteege caaegeeteg    60
gacgcctacc ctagegeetg ceccageget ggegecaatg egtegggee gecaggegeg      120
cggagcgcct cgtccctcgc cctggcaatc gccatcaccg cgctctactc ggccgtgtgc    180
gccgtggggc tgctgggcaa cgtgcttgtc atgttcggca tcgtccggta cactaagatg    240
aagacggcca ccaacatcta catcttcaac ctggccttag ccgatgcgct ggccaccagc    300
acgctgcctt tccagagtgc caagtacctg atggagacgt ggcccttcgg cgagctgctc    360
tgcaaggctg tgctctccat cgactactac aatatgttca ccagcatctt cacgctcacc    420
atgatgagtg ttgaccgcta catcgctgtc tgccaccctg tcaaggccct ggacttccgc    480
acgcctgcca aggccaagct gatcaacatc tgtatctggg tcctggcctc aggcgttggc    540
gtgcccatca tggtcatggc tgtgacccgt ccccgggacg gggcagtggt gtgcatgctc    600
cagttcccca gccccagctg gtactgggac acggtgacca agatctgcgt gttcctcttc    660
gccttcgtgg tgcccatcct catcatcacc gtgtgctatg gcctcatgct gctgcgcctg    720
cgcagtgtgc gcctgctgtc gggctccaag gagaaggacc gcagcctgcg gcgcatcacg    780
cgcatggtgc tggtggttgt gggcgccttc gtggtgtgtt gggcgcccat ccacatcttc    840
gtcatcgtct ggacgctggt ggacatcgac cggcgcgacc cgctggtggt ggctgcgctg    900
cacctgtgca tcgcgctggg ttacgccaat agcagcctca ccccgtgct ctacgctttc    960
ctcgacgaga cttcaagcg ctgcttccgc cagctctgcc gcaagccctg cggccgccca    1020
gaccccagca gcttcagccg cgcccgcgaa gccacggccc gcgagcgtgt caccgcctgc    1080
accccgtccg atggtcccgg cggtggcgct gccgcctga                          1119
```

<210> SEQ ID NO 7
<211> LENGTH: 3564
<212> TYPE: DNA
<213> ORGANISM: Homo sapiens

<400> SEQUENCE: 7

```
ctggaggaaa agaaagtttg ccaaggcacg agtaacaagc tcacgcagtt gggcactttt    60
gaagatcatt ttctcagcct ccagaggatg ttcaataact gtgaggtggt ccttgggaat    120
ttggaaatta cctatgtgca gaggaattat gatctttcct tcttaaagac catccaggag    180
gtggctggtt atgtcctcat tgccctcaac acagtggagc gaattccttt ggaaaacctg    240
cagatcatca gaggaaatat gtactacgaa aattcctatg ccttagcagt cttatctaac    300
tatgatgcaa ataaaccgg actgaaggag ctgcccatga aaatttaca ggaaatcctg    360
catggcgccg tgcggttcag caacaaccct gccctgtgca acgtggagag catccagtgg    420
cgggacatag tcagcagtga ctttctcagc aacatgtcga tggacttcca gaaccacctg    480
ggcagctgcc aaaagtgtga tccaagctgt cccaatggga gctgctgggg tgcaggagag    540
gagaactgcc agaaactgac caaaatcatc tgtgcccagc agtgctccgg gcgctgccgt    600
ggcaagtccc ccagtgactg ctgccacaac cagtgtgctg caggctgcac aggccccgg    660
gagagcgact gcctggtctg ccgcaaattc cgagacgaag ccacgtgcaa ggacacctgc    720
```

```
cccccactca tgctctacaa ccccaccacg taccagatgg atgtgaaccc cgagggcaaa    780
tacagctttg gtgccacctg cgtgaagaag tgtccccgta attatgtggt gacagatcac    840
ggctcgtgcg tccgagcctg tggggccgac agctatgaga tggaggaaga cggcgtccgc    900
aagtgtaaga agtgcgaagg gccttgccgc aaagtgtgta acggaatagg tattggtgaa    960
tttaaagact cactctccat aaatgctacg aatattaaac acttcaaaaa ctgcacctcc   1020
atcagtggcg atctccacat cctgccggtg gcatttaggg gtgactcctt cacacatact   1080
cctcctctgg atccacagga actggatatt ctgaaaaccg taaggaaat cacagggttt    1140
ttgctgattc aggcttggcc tgaaaacagg acggacctcc atgcctttga aacctagaa    1200
atcatacgcg gcaggaccaa gcaacatggt cagttttctc ttgcagtcgt cagcctgaac   1260
ataacatcct tgggattacg ctccctcaag gagataagtg atggagatgt gataatttca   1320
ggaaacaaaa atttgtgcta tgcaaataca ataaactgga aaaaactgtt tgggacctcc   1380
ggtcagaaaa ccaaaattat aagcaacaga ggtgaaaaca gctgcaaggc cacaggccag   1440
gtctgccatg cctgtgctc ccccgagggc tgctggggcc cggagcccaa ggactgcgtc    1500
tcttgccgga atgtcagccg aggcaggaa tgcgtggaca gtgcaacct tctggagggt     1560
gagccaaggg agtttgtgga aactctgag tgcatacagt gccacccaga gtgcctgcct    1620
caggccatga acatcacctg cacaggacgg ggaccagaca actgtatcca gtgtgcccac   1680
tacattgacg gcccccactg cgtcaagacc tgcccggcag gagtcatggg agaaaacaac   1740
accctggtct ggaagtacgc agacgccggc catgtgtgcc acctgtgcca tccaaactgc   1800
acctacggat gcacagggcc aggtcttgaa ggctgtccaa cgaatgggcc taagatcccg   1860
tccatcgcca ctgggatggt gggggccctc ctcttgctgc tggtggtggc cctggggatc   1920
ggcctcttca tgcgaaggcg ccacatcgtt cggaagcgca cgctgcggag gctgctgcag   1980
gagagggagc ttgtggagcc tcttacaccc agtggagaag ctcccaacca agctctcttg   2040
aggatcttga aggaaactga attcaaaaag atcaaagtgc tgggctccgg tgcgttcggc   2100
acggtgtata agggactctg gatcccagaa ggtgagaaag ttaaaattcc cgtcgctatc   2160
aaggaattaa gagaagcaac atctccgaaa gccaacaagg aaatcctcga tgaagcctac   2220
gtgatggcca gcgtggacaa ccccccacgtg tgccgcctgc tgggcatctg cctcacctcc   2280
accgtgcagc tcatcacgca gctcatgccc ttcggctgcc tcctggacta tgtccgggaa   2340
cacaaagaca atattggctc ccagtacctg ctcaactggt gtgtgcagat cgcaaagggc   2400
atgaactact ggaggaccg tcgcttggtg caccgcgacc tggcagccag gaacgtactg   2460
gtgaaaacac cgcagcatgt caagatcaca gattttgggc tggccaaact gctgggtgcg   2520
gaagagaaag aataccatgc agaaggaggc aaagtgccta tcaagtggat ggcattggaa   2580
tcaattttac acagaatcta tacccaccag agtgatgtct ggagctacgg ggtgaccgtt   2640
tgggagttga tgacctttgg atccaagcca tatgacggaa tccctgccag cgagatctcc   2700
tccatcctgg agaaaggaga acgcctccct cagccaccca tatgtaccat cgatgtctac   2760
atgatcatgg tcaagtgctg gatgatagac gcagatagtc gcccaaagtt ccgtgagttg   2820
atcatcgaat tctccaaaat ggcccgagac ccccagcgct accttgtcat tcaggggat    2880
gaaagaatgc atttgccaag tcctacagac tccaacttct accgtgccct gatggatgaa   2940
gaagacatgg acgacgtggt ggatgccgac gagtacctca tcccacagca gggcttcttc   3000
agcagcccct ccacgtcacg gactcccctc ctgagctctc tgagtgcaac cagcaacaat   3060
tccaccgtgg cttgcattga tagaaatggg ctgcaaagct gtcccatcaa ggaagacagc   3120
```

| | |
|---|---|
| ttcttgcagc gatacagctc agacccaca ggcgccttga ctgaggacag catagacgac | 3180 |
| accttcctcc cagtgcctga atacataaac cagtccgttc ccaaaaggcc cgctggctct | 3240 |
| gtgcagaatc ctgtctatca caatcagcct ctgaaccccg cgcccagcag agacccacac | 3300 |
| taccaggacc cccacagcac tgcagtgggc aaccccgagt atctcaacac tgtccagccc | 3360 |
| acctgtgtca acagcacatt cgacagccct gcccactggg cccagaaagg cagccaccaa | 3420 |
| attagcctgg acaaccctga ctaccagcag gacttctttc caaggaagc caagccaaat | 3480 |
| ggcatcttta agggctccac agctgaaaat gcagaatacc taagggtcgc gccacaaagc | 3540 |
| agtgaattta ttggagcagt ttaa | 3564 |

<210> SEQ ID NO 8
<211> LENGTH: 1149
<212> TYPE: DNA
<213> ORGANISM: Homo sapiens

<400> SEQUENCE: 8

| | |
|---|---|
| atggggccca ccagcgtccc gctggtcaag gcccaccgca gctcggtctc tgactacgtc | 60 |
| aactatgata tcatcgtccg gcattacaac tacacgggaa agctgaatat cagcgcggac | 120 |
| aaggagaaca gcattaaact gacctcggtg gtgttcattc tcatctgctg ctttatcatc | 180 |
| ctggagaaca tctttgtctt gctgaccatt tggaaaacca agaaattcca ccgacccatg | 240 |
| tactatttta ttggcaatct ggccctctca gacctgttgg caggagtagc ctacacagct | 300 |
| aacctgctct gtctggggc caccacctac aagctcactc ccgcccagtg gtttctgcgg | 360 |
| gaagggagta tgtttgtggc cctgtcagcc tccgtgttca gtctcctcgc catcgccatt | 420 |
| gagcgctata tcacaatgct gaaaatgaaa ctccacaacg ggagcaataa cttccgcctc | 480 |
| ttcctgctaa tcagcgcctg ctgggtcatc tccctcatcc tgggtggcct gcctatcatg | 540 |
| ggctggaact gcatcagcgc gctgtccagc tgctccaccg tgctgccgct ctaccacaag | 600 |
| cactatatcc tcttctgcac cacggtcttc actctgcttc tgctctccat cgtcattctg | 660 |
| tactgcagaa tctactcctt ggtcaggact cggagccgcc gcctgacgtt ccgcaagaac | 720 |
| atttccaagg ccagccgcag ctctgagaag tcgctggcgc tgctcaagac cgtaattatc | 780 |
| gtcctgagcg tcttcatcgc ctgctgggca ccgctcttca tcctgctcct gctggatgtg | 840 |
| ggctgcaagg tgaagacctg tgacatcctc ttcagagcgg agtacttcct ggtgttagct | 900 |
| gtgctcaact ccggcaccaa ccccatcatt tacactctga ccaacaagga gatgcgtcgg | 960 |
| gccttcatcc ggatcatgtc ctgctgcaag tgcccgagcg agactctgc tggcaaattc | 1020 |
| aagcgaccca tcatcgccgg catggaattc agccgcagca atcggacaa ttcctcccac | 1080 |
| ccccagaaag acgaaggga caacccagag accattatgt cttctggaaa cgtcaactct | 1140 |
| tcttcctag | 1149 |

<210> SEQ ID NO 9
<211> LENGTH: 1110
<212> TYPE: DNA
<213> ORGANISM: Homo sapiens

<400> SEQUENCE: 9

| | |
|---|---|
| ctcatggcgt ccaccacttc cgctgtgcct gggcatccct ctctgcccag cctgcccagc | 60 |
| aacagcagcc aggagaggcc actggacacc cggaccccgc tgctagcccg ggcggagctg | 120 |
| gcgctgctct ccatagtctt tgtggctgtg gccctgagca atggcctggt gctggcggcc | 180 |

| | |
|---|---|
| ctagctcggc ggggccggcg gggccactgg gcacccatac acgtcttcat tggccacttg | 240 |
| tgcctggccg acctgccgt ggctctgttc caagtgctgc cccagctggc ctggaaggcc | 300 |
| accgaccgct tccgtgggcc agatgccctg tgtcgggccg tgaagtatct gcagatggtg | 360 |
| ggcatgtatg cctcctccta catgatcctg gccatgacgc tggaccgcca ccgtgccatc | 420 |
| tgccgtccca tgctggcgta ccgccatgga agtggggctc actggaaccg gccggtgcta | 480 |
| gtggcttggg ccttctcgct ccttctcagc ctgccccagc tcttcatctt cgcccagcgc | 540 |
| aacgtggaag gtggcagcgg ggtcactgac tgctgggcct gctttgcgga gccctggggc | 600 |
| cgtcgcacct atgtcacctg gattgccctg atggtgttcg tggcacctac cctgggtatc | 660 |
| gccgcctgcc aggtgctcat cttccgggag attcatgcca gtctggtgcc agggccatca | 720 |
| gagaggcctg gggggcgccg caggggacgc cggacaggca gccccggtga gggagcccac | 780 |
| gtgtcagcag ctgtggccaa gactgtgagg atgacgctag tgattgtggt cgtctatgtg | 840 |
| ctgtgctggg cacccttctt cctggtgcag ctgtgggccg cgtgggaccc ggaggcacct | 900 |
| ctggaagggg cgccctttgt gctactcatg ttgctggcca gcctcaacag ctgcaccaac | 960 |
| ccctggatct atgcatcttt cagcagcagc gtgtcctcag agctgcgaag cttgctctgc | 1020 |
| tgtgcccggg gacgcacccc acccagcctg ggtccccaag atgagtcctg caccaccgcc | 1080 |
| agctcctccc tggccaagga cacttcatcg | 1110 |

<210> SEQ ID NO 10
<211> LENGTH: 1239
<212> TYPE: DNA
<213> ORGANISM: Homo sapiens

<400> SEQUENCE: 10

| | |
|---|---|
| gggcaacccg ggaacggcag cgccttcttg ctggcaccca atagaagcca tgcgccggac | 60 |
| cacgacgtca cgcagcaaag ggacgagtg tgggtggtgg gcatgggcat cgtcatgtct | 120 |
| ctcatcgtcc tggccatcgt gtttggcaat gtgctggtca tcacagccat tgccaagttc | 180 |
| gagcgtctgc agacggtcac caactacttc atcacttcac tggcctgtgc tgatctggtc | 240 |
| atgggcctgg cagtggtgcc cttttggggcc gcccatattc ttatgaaaat gtggactttt | 300 |
| ggcaacttct ggtgcgagtt ttggacttcc attgatgtgc tgtgcgtcac ggccagcatt | 360 |
| gagaccctgt gcgtgatcgc agtggatcgc tactttgcca ttacttcacc tttcaagtac | 420 |
| cagagcctgc tgaccaagaa taaggcccgg gtgatcattc tgatggtgtg gattgtgtca | 480 |
| ggccttacct ccttcttgcc cattcagatg cactggtacc gggccaccca ccaggaagcc | 540 |
| atcaactgct atgccaatga gacctgctgt gacttcttca cgaaccaagc ctatgccatt | 600 |
| gcctcttcca tcgtgtcctt ctacgttccc ctggtgatca tggtcttcgt ctactccagg | 660 |
| gtctttcagg aggccaaaag gcagctccag aagattgaca atctgagggg ccgcttccat | 720 |
| gtccagaacc ttagccaggt ggagcaggat gggcggacgg gcatggact ccgcagatct | 780 |
| tccaagttct gcttgaagga gcacaaagcc ctcaagacgt taggcatcat catgggcact | 840 |
| ttcaccctct gctggctgcc cttcttcatc gttaacattg tgcatgtgat ccaggataac | 900 |
| ctcatccgta aggaagttta catcctccta aattggatag ctatgtcaa ttctggtttc | 960 |
| aatccccctta tctactgccg gagcccagat ttcaggattg ccttccagga gcttctgtgc | 1020 |
| ctgcgcaggt cttcttttgaa ggcctatggg aatggctact ccagcaacgg caacacaggg | 1080 |
| gagcagagtg gatatcacgt ggaacaggag aaagaaaata aactgctgtg tgaagacctc | 1140 |
| ccaggcacgg aagactttgt gggccatcaa ggtactgtgc ctagcgataa cattgattca | 1200 | caagggagga attgtagtac aaatgactca ctgctgtaa            1239

<210> SEQ ID NO 11
<211> LENGTH: 1623
<212> TYPE: DNA
<213> ORGANISM: Artificial Sequence
<220> FEATURE:
<223> OTHER INFORMATION: Synthetic

<400> SEQUENCE: 11
gccaaaaaca ttaagaaggg cccagcgcca ttctacccac tcgaagacgg gaccgccggc      60
gagcagctgc acaaagccat gaagcgctac gccctggtgc ccggcaccat cgcctttacc     120
gacgcacata tcgaggtgga cattacctac gccgagtact tcgagatgag cgttcggctg     180
gcagaagcta tgaagcgcta tgggctgaat acaaaccatc ggatcgtggt gtgcagcgag     240
aatagcttgc agttcttcat gcccgtgttg ggtgccctgt tcatcggtgt ggctgtggcc     300
ccagctaacg acatctacaa cgagcgcgag ctgctgaaca gcatgggcat cagccagccc     360
accgtcgtat tcgtgagcaa gaaagggctg caaaagatcc tcaacgtgca aaagaagcta     420
ccgatcatac aaaagatcat catcatggat agcaagaccg actaccaggg cttccaaagc     480
atgtacacct tcgtgacttc ccatttgcca cccggcttca acgagtacga cttcgtgccc     540
gagagcttcg accgggacaa aaccatcgcc ctgatcatga acagtagtgg cagtaccgga     600
ttgcccaagg gcgtagccct accgcaccgc accgcttgtg tccgattcag tcatgcccgc     660
gaccccatct tcggcaacca gatcatcccc gacaccgcta tcctcagcgt ggtgccattt     720
caccacggct tcggcatgtt caccacgctg gctacttga tctgcggctt tcgggtcgtg     780
ctcatgtacc gcttcgagga ggagctattc ttgcgcagct tgcaagacta taagattcaa     840
tctgccctgc tggtgcccac actatttagc ttcttcgcta agagcactct catcgacaag     900
tacgaccta gcaacttgca cgagatcgcc agcggcgggg cgccgctcag caaggaggta     960
ggtgaggccg tggccaaacg cttccaccta ccaggcatcc gccagggcta cggcctgaca    1020
gaaacaacca gcgccattct gatcacccc gaagggacg acaagcctgg cgcagtaggc    1080
aaggtggtgc ccttcttcga ggctaaggtg gtggacttgg acaccggtaa gacactgggt    1140
gtgaaccagc gcggcgagct gtgcgtccgt ggccccatga tcatgagcgg ctacgttaac    1200
aaccccgagg ctacaaacgc tctcatcgac aaggacggct ggctgcacag cggcgacatc    1260
gcctactggg acgaggacga gcacttcttc atcgtggacc ggctgaagag cctgatcaaa    1320
tacaagggct accaggtagc cccagccgaa ctggagagca tcctgctgca acaccccaac    1380
atcttcgacg ccggggtcgc cggcctgccc gacgacgatg ccggcgagct gcccgccgca    1440
gtcgtcgtgc tggaacacgg taaaaccatg accgagaagg agatcgtgga ctatgtggcc    1500
agccaggtta caaccgccaa gaagctgcgc ggtggtgttg tgttcgtgga cgaggtgcct    1560
aaaggactga ccggcaagtt ggacgcccgc aagatccgcg agattctcat taaggccaag    1620
aag                                                                  1623

<210> SEQ ID NO 12
<211> LENGTH: 513
<212> TYPE: DNA
<213> ORGANISM: Artificial Sequence
<220> FEATURE:
<223> OTHER INFORMATION: Synthetic

<400> SEQUENCE: 12

-continued

```
atggtgttta cattggagga tttcgttgga gactggcggc agacagctgg atacaaccaa         60
gatcaagtgt tagaacaagg aggattgtct agtctgttcc aaaagctggg agtgtcagtc        120
accccaatcc agaaaattgt gctgtctggg gagaatgggt taaaaattga tattcatgtc        180
atcatccctt acgagggact cagtggtttt caaatgggtc tgattgaaat gatcttcaaa        240
gttgtttacc cagtggatga tcatcatttc aaggttattc tccattatgg tacactcgtt        300
attgacggtg tgacaccaaa catgattgac tactttggac gcccttacga gggaattgct        360
gtgtttgacg gcaagaagat cacagttact ggaactctgt ggaacggcaa caagatcatt        420
gatgagcgcc tgatcaaccc agatggttca ctcctcttcc gcgttactat caatggagtc        480
accggatggc gcctttgcga gcgtattctt gcc                                    513
```

COMPOSITIONS AND METHODS FOR MONITORING TRANSMEMBRANE TRAFFICKING

This application claims is a divisional of U.S. patent application Ser. No. 13/683,662, filed Nov. 21, 2012, which claims priority to U.S. Provisional Patent Application Ser. No. 61/563,294, filed Nov. 23, 2011, each of which is herein incorporated by reference in its entirety.

FIELD

Provided herein are compositions and methods for monitoring the movement of analytes and/or cellular components across biological membranes (e.g., cell surface internalization). In particular, reporter constructs are provided, the transmembrane movement of which (e.g., by endocytosis), is monitored by methods described herein.

BACKGROUND

Endocytosis is a critical mechanism central to, among other processes, receptor desensitization and signal transduction. Available technologies for measuring endocytosis based upon high-content imaging are biologically predictive, but limited in terms of ease of use. In contrast, high throughput screening (HTS)-compatible technologies, such as those utilizing enzyme fragment complementation, require excessive engineering of the biological system, often leading to screening errors (e.g., false negative hits in HTS).

SUMMARY

In some embodiments, the present invention provides methods of detecting endocytosis comprising: (a) tethering a reporter element to a cell-surface analyte to create a fusion element; and (b) monitoring a detectable signal from the reporter element thereby detecting endocytosis. In some embodiments, the reporter element emits the detectable signal upon interaction with a reporter substrate. In some embodiments, the method further comprises a step between steps (a) and (b) of contacting the reporter element with a reporter substrate. In some embodiments, the method further comprises a step between steps (a) and (b) of allowing endocytosis of the cell-surface analyte, the reporter element, and/or the fusion element. In some embodiments, the detectable signal from the reporter element is altered upon endocytosis of the reporter element. In some embodiments, monitoring the detectable signal thereby detecting endocytosis comprises: (i) allowing endocytosis of the fusion element; and (ii) detecting the signal after induction of endocytosis. In some embodiments, monitoring the detectable signal to detect endocytosis comprises: (i) detecting the signal from the reporter element prior to endocytosis; (ii) allowing endocytosis of the fusion element; (iii) repeating detection of the signal from the reporter element; and (iv) comparing the signal from step (i) to the signal from step (iii) to detect endocytosis. In some embodiments, allowing endocytosis of the fusion element comprises allowing time (e.g., sufficient time) for endocytosis to occur (e.g., 1 sec . . . 2 sec . . . 5 sec . . . 30 sec . . . 1 min 2 min . . . 5 min . . . 30 min . . . 60 min, or more). In some embodiments, the cell-surface analyte is a cell surface component. In some embodiments, the cell surface component comprises a cell surface receptor. In some embodiments, the cell-surface analyte is non-covalently associated with a component of the cell surface. In some embodiments, the reporter element and the cell-surface analyte are expressed as a fusion protein. In some embodiments, the reporter element and the cell-surface analyte are covalently or non-covalently coupled (e.g., after translation). In some embodiments, the reporter element and the cell-surface analyte are expressed as a fusion protein. In some embodiments, the detectable signal comprises an optical signal. In some embodiments, the detectable signal comprises luminescence. In some embodiments, the reporter element comprises a luciferase enzyme. In some embodiments, the luciferase enzyme is a beetle or Oplophorus luciferase enzyme. In some embodiments, a luciferase enzyme is a wild-type luciferase (e.g., beetle or Oplophorus luciferase enzyme) or a mutant thereof (e.g., >70% sequence identity to wild-type). In some embodiments, endocytosis results in movement of the reporter element from the extracellular space to the intracellular space. In some embodiments, the reporter element moves across a biological membrane (e.g., plasma membrane). In some embodiments, the reporter element translocates into a new membrane microenvironment. In some embodiments, the detectable signal is detectably altered (e.g., gain of signal, reduction of signal, change in emission property, etc.) within the intracellular space compared to the extracellular space. In some embodiments, the detectable signal from the reporter is reduced within the intracellular space compared to the extracellular space. In some embodiments, the intracellular space comprises an endosome. In some embodiments, the detectable signal is detectably altered (e.g., gain of signal, reduction of signal, change in emission property, etc.) within the endosome compared to the extracellular space. In some embodiments, the detectable signal from the reporter is reduced within the endosome compared to the outside of the cell. In some embodiments, the method further comprises a step between steps (i) and (ii) of triggering endocytosis. In some embodiments, endocytosis is triggered by one or more of: receptor agonists (e.g., small molecule, cytokines, etc.), modified growth conditions, pharmacologic compounds, changes in cellular signaling pathways, presence of any endocytosis inducing species, etc. In some embodiments, the reporter substrate is permeable to the plasma membrane of live cells. In some embodiments, the reporter substrate is permeable to cellular membranes. In some embodiments, the reporter substrate is completely or largely excluded from the intracellular space of the cell. In some embodiments, the reporter is capable of turning over multiple reporter substrates (e.g., multiple substrate turnover). In some embodiments, the reporter substrate is a luciferin, luciferin derivative, coelenterazine, or a coelenterazine derivative.

In some embodiments, the present invention provides methods of detecting endocytosis comprising: (a) incorporating a fusion element into the cell membrane of a cell, wherein the fusion element comprises a cell-surface analyte and a reporter element; (b) contacting the reporter with a reporter substrate, wherein the contacting produces a detectable signal; and (c) monitoring the detectable signal thereby detecting endocytosis. In some embodiments, monitoring of the detectable signal comprises: (i) allowing endocytosis of the fusion element; and (ii) detecting the signal after induction of endocytosis. In some embodiments, monitoring of the detectable signal comprises: (i) detecting the signal prior to endocytosis; (ii) allowing endocytosis of the fusion element; (iii) detecting the signal following endocytosis; and (iv) comparing the signal from step (i) to the signal from step (iii) to detect endocytosis. In some embodiments, the fusion element comprises a fusion protein. In some embodiments, allowing endocytosis comprises allowing time (e.g., sufficient time) for endocytosis to occur (e.g., 1 sec . . . 2 sec . . . 5 sec . . . 30 sec . . . 1 min . . . 2 min . . . 5 min . . . 30 min . . . 60 min, or more). In some embodiments, the cell-surface analyte comprises a cell surface component. In some embodiments, the cell surface component comprises a cell surface receptor. In some embodiments, the cell-surface analyte is non-covalently associated with a component of the cell surface. In some embodiments, the reporter element comprises a luciferase enzyme. In some embodiments, the luciferase enzyme is a beetle or *Oplophorus* luciferase enzyme. In some embodiments, the luciferase enzyme is a wild-type enzyme (e.g., beetle or *Oplophorus* luciferase enzyme) or a mutant thereof (e.g., >70% sequence identity). In some embodiments, the fusion element is incorporated into the cell membrane such that the reporter element is localized in the extracellular space (e.g., adjacent to the cell). In some embodiments, endocytosis of the reporter element results in movement of the reporter element from an extracellular space into an endosome. In some embodiments, the signal is detectably altered within the endosome compared to the extracellular space. In some embodiments, the signal is reduced within the endosome compared to the extracellular space. In some embodiments, the method further comprises a step between steps (i) and (ii) of triggering endocytosis. In some embodiments, endocytosis is triggered by one or more of: receptor agonists (e.g., small molecule, cytokines, etc.), modified growth conditions, pharmacologic compounds, changes in cellular signaling pathways, presence of any endocytosis inducing species, etc. In some embodiments, the reporter substrate is known to be permeable to the plasma membrane of live cells. In some embodiments, the reporter substrate is permeable to cellular membranes or is completely or largely excluded from the topological inside of the cell under the conditions of the experiment. In some embodiments, the reporter substrate is a luciferin, luciferin derivative, coelenterazine or coelenterazine derivative.

In some embodiments, the present invention provides methods of detecting endocytosis comprising one or more of the steps of (e.g., all of the steps, all of the steps in order): (a) incorporating a fusion protein into the cell membrane of a cell, wherein the fusion protein comprises a reporter polypeptide and a cell surface receptor, wherein the reporter polypeptide emits a detectable signal upon interaction with a reporter substrate; (b) contacting the reporter polypeptide with the reporter substrate; (c) detecting the detectable signal; (d) inducing endocytosis and/or allowing endocytosis to occur; (e) repeating detection of the detectable signal; and (f) comparing the signal from step (c) to the signal from step (e), wherein alteration of the signal indicates that endocytosis occurred. In some embodiments, the fusion protein is expressed from a fusion construct. In some embodiments, the fusion protein is generated based upon antibody-antigen association. In some embodiments, the fusion protein is expressed within the cell. In some embodiments, the cell-surface analyte is produced exogenously and added to the medium of the cell. In some embodiments, the reporter substrate is cell membrane permeable. In some embodiments, the reporter polypeptide is capable of multiple turnovers of the reporter substrate. In some embodiments, the reporter polypeptide comprises a luciferase enzyme. In some embodiments, the luciferase enzyme is a beetle or *Oplophorus* luciferase enzyme. In some embodiments, the luciferase enzyme is a wild-type enzyme (e.g., beetle or *Oplophorus* luciferase enzyme) or a mutant thereof (e.g., >70% sequence identity). In some embodiments, the fusion protein is incorporated into the cell membrane such that the reporter element is localized to the outside of the cell. In some embodiments, endocytosis of the reporter polypeptide results in movement of the reporter polypeptide from an extracellular space into an intracellular space. In some embodiments, the signal is detectably altered within the intracellular space compared to the extracellular space. In some embodiments, the intracellular space into is an endosome. In some embodiments, the signal is detectably altered within the endosome compared to the extracellular space. In some embodiments, the signal is reduced within the intracellular space compared to the extracellular space. In some embodiments, the signal is reduced within the endosome compared to the extracellular space. In some embodiments, the reporter substrate is known to be permeable to the plasma membrane of live cells. In some embodiments, the reporter substrate is permeable to cellular membranes or is completely or largely excluded from the topological inside of the cell under the conditions of the experiment. In some embodiments, the reporter substrate is a luciferin, luciferin derivative, coelenterazine or coelenterazine derivative.

In some embodiments, the present invention provides compositions and methods of detecting endocytosis comprising: (a) tethering a reporter element to a cell-surface analyte; and (b) monitoring a detectable signal from the reporter element thereby detecting endocytosis. In some embodiments, the reporter element emits a detectable signal upon interaction with a reporter substrate. In some embodiments, the method further comprises a step between steps (a) and (b) of contacting the reporter element with a reporter substrate. In some embodiments, the method further comprises a step between steps (a) and (b) of allowing time for the endocytosis of the cell-surface analyte and/or the reporter element. In some embodiments, the detectable signal from the reporter element is altered upon endocytosis of the reporter element. In some embodiments, monitoring the detectable signal to detect endocytosis comprises: (i) allowing endocytosis of the fusion element and (ii) detecting the signal induction of endocytosis. In some embodiments, monitoring the detectable signal to detect endocytosis comprises: (i) detecting the signal prior to endocytosis; (ii) allowing endocytosis of the fusion element; (iii) detecting the signal following endocytosis; and (iv) comparing the signal from step (i) to the signal from step (iii) thereby detecting endocytosis. In some embodiments, the reporter element is tethered to a cell surface component. In some embodiments, the cell surface component comprises a cell surface receptor. In some embodiments, a cell surface receptor comprises a sequence of SEQ ID NO. 5, SEQ ID NO. 6, SEQ ID NO. 7, SEQ ID NO. 8, SEQ ID NO. 9, or SEQ ID NO. 10. In some embodiments, a cell surface receptor comprises greater that 70% sequence identity (e.g., 75% . . . 80% . . . 90% . . . 95% . . . 98% . . . 99%) with one of SEQ ID NOS. 5-10. In some embodiments, a cell surface receptor retains all or a portion of the biological activity of one of SEQ ID NOS. 5-10. In some embodiments, the reporter element and the cell surface component are expressed as a fusion protein. In some embodiments, a fusion protein comprises one or more peptide elements in addition to the reporter element and the cell surface component. In some embodiments, a fusion protein comprises one or more signal peptides (e.g., IL6 signal peptide). In some embodiments, a fusion protein comprises a signal peptide of 70% or greater sequence identity (e.g., 70% . . . 80% . . . 90% . . . 95% . . . 98% . . . 99%) with SEQ ID NO. 1. In some embodiments, a fusion protein comprises one or more linker segments (e.g., GSSG linker). In some embodiments, a linker segment is a peptide or non-peptide (e.g.

nucleic acid, PEG, alkyl chain) segment connecting two polypeptide portions of the fusion protein. In some embodiments, a fusion protein comprises a linker of 70% or greater sequence identity (e.g., 70% . . . 80% . . . 90% . . . 95% . . . 98% . . . 99%) with SEQ ID NO. 2. In some embodiments, the detectable signal comprises an optical signal. In some embodiments, the detectable signal comprises luminescence. In some embodiments, the reporter element comprises a luciferase enzyme. In some embodiments the luciferase enzyme comprises a sequence of SEQ ID NO. 3 or SEQ ID NO. 4. In some embodiments, the luciferase enzyme comprises greater that 70% sequence identity (e.g., 75% . . . 80% . . . 90% . . . 95% . . . 98% . . . 99%) with one of SEQ ID NOS. 3-4. In some embodiments, the luciferase enzyme retains all or a portion of the biological activity of one of SEQ ID NOS. 3-4. In some embodiments, endocytosis results in movement of the reporter element from the outside of the cell into an endosome. In some embodiments, endocytosis results in movement of the reporter element from the extracellular space into an intracellular space (e.g., an endosome). In some embodiments, the detectable signal is detectably altered within the endosome compared to the outside of the cell. In some embodiments, the detectable signal from the reporter element is reduced within the endosome compared to the outside of the cell. In some embodiments, the method further comprises a step between steps (i) and (ii) of triggering endocytosis (e.g., with a chemical (e.g., with a pharmaceutical agent)). In some embodiments, the reporter substrate is added to the cell medium. In some embodiments, the reporter substrate is permeable to the plasma membrane of live cells, is permeable to cell membranes, or is completely or largely excluded from the topological inside of the cell.

In some embodiments, the present invention provides methods of detecting endocytosis comprising: (a) incorporating a fusion element into the cell membrane of a cell, wherein the fusion element comprises an cell-surface analyte and a reporter element; (b) contacting the reporter element with a reporter substrate, wherein the contacting produces a signal from the reporter element; and (c) monitoring the signal thereby detecting endocytosis. In some embodiments, monitoring the signal to detect endocytosis comprises: (i) detecting the signal prior to endocytosis; (ii) allowing endocytosis of the fusion element and cell-surface analyte; (iii) detecting the signal following endocytosis; and (iv) comparing the signal from step (i) to the signal from step (iii) thereby detecting endocytosis. In some embodiments, the fusion element comprises a fusion protein. In some embodiments, the cell-surface analyte comprises a cell surface component. In one embodiment, the cell surface component comprises a cell surface receptor. In some embodiments, the reporter element comprises a luciferase enzyme (e.g., beetle or *Oplophorus* luciferase enzyme). In some embodiments, the luciferase enzyme is a wild-type enzyme (e.g., beetle or *Oplophorus* luciferase enzyme) or a mutant thereof (e.g., >70% sequence identity). In some embodiments, the fusion element is incorporated into the cell membrane such that the reporter element is localized to the outside of the cell. In some embodiments, endocytosis of the reporter element results in movement of the reporter element from the outside the cell into an endosome. In some embodiments, the signal is detectably altered within the endosome compared to the outside of the cell. In some embodiments, the signal is reduced within the endosome compared to the outside of the cell. In some embodiments, the emission property, e.g., wavelength, of the signal is altered within the endosome compared to outside the cell. In some embodiments, the method further comprises a step between steps (i) and (ii) of triggering endocytosis. In some embodiments, the reporter substrate is permeable to the plasma membrane of live cells, is permeable to cell membranes, or is completely or largely excluded from the topological inside of the cell. In some embodiments, the reporter substrate is a membrane-permeable substrate.

In some embodiments, the present invention provides methods of detecting endocytosis comprising: (a) incorporating a fusion element into the cell membrane of a cell, wherein the fusion element comprises an cell-surface analyte and a reporter element; (b) allowing endocytosis to occur and/or inducing endocytosis; (c) contacting the reporter element with a reporter substrate, wherein the contacting produces a signal from the reporter element; and (d) monitoring the signal thereby detecting endocytosis.

In some embodiments, the present invention provides methods of detecting endocytosis comprising: (a) incorporating a fusion protein into the cell membrane of a cell, wherein the fusion protein comprises a reporter polypeptide and a cell-surface receptor, wherein the reporter polypeptide emits a detectable signal upon interaction with a reporter substrate; (b) contacting the reporter polypeptide with the reporter substrate; (c) detecting the detectable signal from the reporter polypeptide; (d) inducing endocytosis and/or allowing endocytosis to occur; (e) repeating detection of the detectable signal; and (f) comparing the signal from step (c) to the signal from step (e), wherein alteration of the signal indicates that endocytosis occurred. In some embodiments, the fusion protein is expressed from a fusion construct. In some embodiments, the fusion protein is expressed endogenously within the cell. In some embodiments, the fusion protein is expressed exogenously and added to the cell medium.

In some embodiments, the present invention provides fusion proteins comprising a reporter protein and cell surface component, and methods of use thereof, e.g., for detecting endocytosis. In some embodiments, a reporter protein is a reporter enzyme. In some embodiments, the reporter enzyme is a luciferase. In some embodiments, the luciferase is a firefly luciferase, *Oplophorus* luciferase, *Renilla* luciferase, variants or mutants thereof, or other suitable luciferase. In some embodiments, the luciferase has 70% or greater sequence identity to all or a portion of SEQ ID NO. 3 or SEQ ID NO. 4. In some embodiments, the luciferase has the biological activity of a luciferase of SEQ ID NO. 3, SEQ ID NO. 6, SEQ ID NO. 7, SEQ ID NO. 8, SEQ ID NO. 9, or SEQ ID NO. 10. In some embodiments, the luciferase has the biological activity of a luciferase of SEQ ID NO. 3 or SEQ ID NO. 4. In some embodiments, a cell surface component is a cell surface protein. In some embodiments, the cell surface protein is a cell surface receptor. In some embodiments, the cell surface receptor has 70% or greater sequence identity to all or a portion of SEQ ID NO. 3, SEQ ID NO. 6, SEQ ID NO. 7, SEQ ID NO. 8, SEQ ID NO. 9,or SEQ ID NO. 10. In some embodiments, a fusion protein comprises one or more signal peptides (e.g., cell surface signals, secretion signals, etc.). In some embodiments, the signal peptide has 70% or greater sequence identity to all or a portion of SEQ ID NO. 1. In some embodiments, the signal peptide has the biological activity of a signal peptide of SEQ ID NO. 1. In some embodiments, a fusion protein comprises one or more linker segments. In some embodiments, the linker segment is a peptide or non-peptide. In some embodiments, the linker segment is a polymer. In some embodiments, the linker segment is a carbon-containing chain. In some embodiments, the linker is a GSSG linker. In some embodiments, the linker comprises 70% or greater sequence identity to all or a portion of SEQ ID NO. 2. In some embodiments, the linker covalently connects a cell surface component, reporter, and/or signal peptide with one or more of a cell surface component, reporter element, and/or signal peptide. In some embodiments, a secretion tag (e.g., IL6 secretion tag (e.g., SEQ ID NO. 1)) and linker (e.g., GSSG linker (e.g., SEQ ID NO. 2)) are at the N-terminus of the fusion protein. In some embodiments, the secretion tag is attached to the N-terminus of a luciferase reporter enzyme by a linker. In some embodiments, the C-terminal end of a luciferase reporter enzyme is attached to the N-terminal end of a cell surface component, e.g., a cell surface protein or receptor, either directly or by a linker.

In some embodiments, the fusion protein comprises the following formula:

N-Signal Peptide—$L_1$—Reporter—$L_2$—Cell Surface Protein-C;

wherein $L_1$ is an optional linker segment and $L_2$ is a second optional linker segment.

In some embodiments, the fusion protein comprises the following formula:

N-Reporter—L—Cell Surface Protein-C;

wherein L is an optional linker segment.

In some embodiments, the fusion protein comprises the following formula:

N-Signal Peptide—Reporter—Cell Surface Protein-C.

In some embodiments, the fusion protein comprises the following formula:

N-Reporter—Cell Surface Protein-C.

In some embodiments, the fusion protein comprises the following formula:

N-Signal Peptide—$L_1$—Cell Surface Protein—$L_2$—Reporter-C;

wherein $L_1$ is an optional linker segment, and $L_2$ is a second optional linker segment.

In some embodiments, the fusion protein comprises the following formula:

N-Cell Surface Protein—L—Reporter-C;

wherein L is an optional linker segment.

In some embodiments, the fusion protein comprises the following formula:

N-Signal Peptide—Cell Surface Protein—Reporter-C;

wherein $L_1$ is an optional linker segment, and $L_2$ is a second optional linker segment.

In some embodiments, the fusion protein comprises the following formula:

N-Cell Surface Protein—Reporter-C

In some embodiments, the present invention provides kits comprising components, reagents (e.g., fusion constructs, reporter proteins, substrates, etc.), materials (e.g., solid supports (e.g., multiwell plates), cells), and/or systems/devices (e.g., fluorometers, cell imaging, data analysis, etc.), for performing assays described herein. In some embodiments, for example, a kit of the present invention may comprise a fusion construct comprising a reporter protein, e.g., a luciferase enzyme, and a substrate for the reporter protein, e.g., a luciferin or coelenterazine or derivatives thereof.

In some embodiments, the present invention provides methods of detecting transmembrane trafficking comprising: (a) incorporating a fusion protein into a membrane of a cell, wherein the fusion protein comprises a reporter element and a membrane-associated element, wherein the reporter element emits a detectable signal upon interaction with a reporter substrate; (b) contacting the reporter element with the reporter substrate; and (c) detecting the detectable signal. In some embodiments, the method further comprises the steps of: (d) inducing transmembrane trafficking and/or allowing transmembrane trafficking to occur; (e) repeating detection of the detectable signal; and (f) comparing the signal from step (c) to the signal from step (e), wherein alteration of the signal indicates that transmembrane trafficking occurred. In some embodiments, the method further comprises a step between steps (a) and (b) inducing endocytosis and/or allowing transmembrane trafficking to occur. In some embodiments, the method further comprises: (f) comparing the signal from step (c) to a control signal, wherein alteration of the signal indicates that transmembrane trafficking occurred. In some embodiments, the reporter element is an enzyme. In some embodiments, the signal is an optical signal. In some embodiments, the reporter substrate is membrane permeable. In some embodiments, the membrane-associated element is a membrane-associate polypeptide.

DEFINITIONS

Figure 1A:
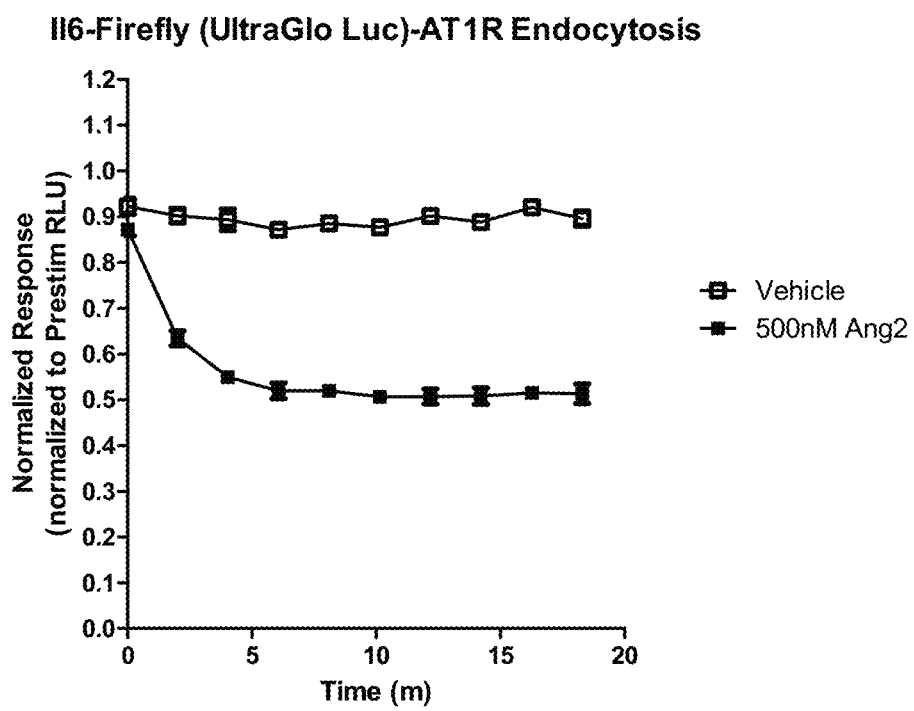
FIGS. 1A-D show graphs depicting kinetic measurements of the endocytosis of fusion proteins of GPCRs fused to firefly luciferase in response to agonist or vehicle-only: (A) Firefly-Luc/AT1R internalization, (B) Firefly-Luc/OPRD1 internalization, (C) Firefly-Luc/B2AR internalization, and (D) Firefly-Luc/V2R internalization.
Figure 1B:
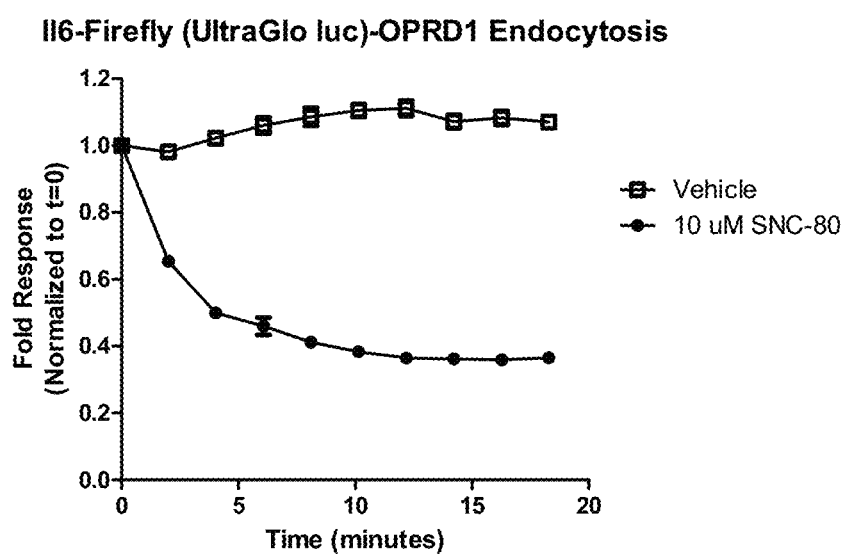
Figure 1C:
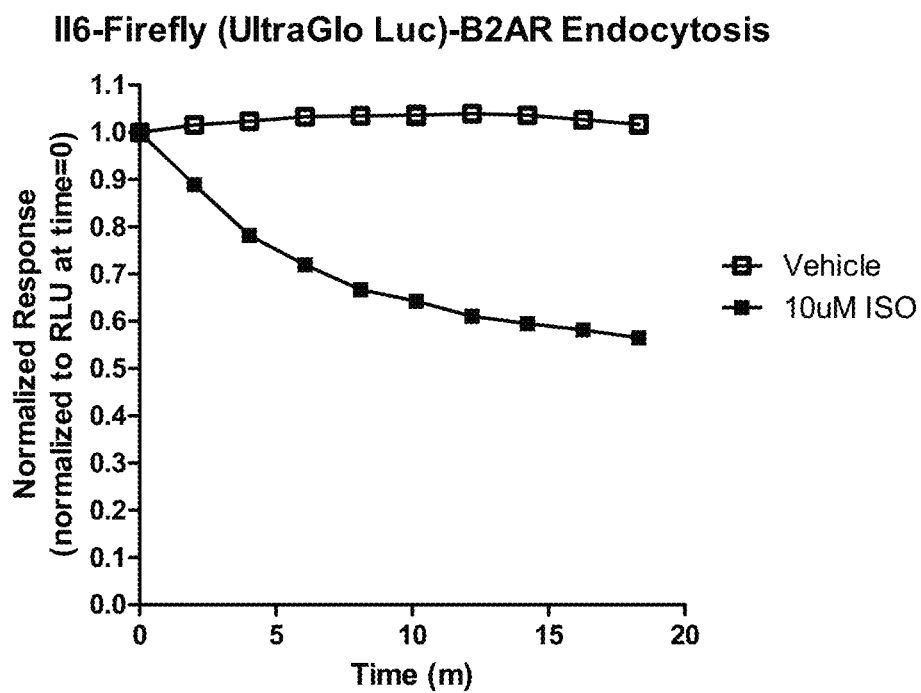
Figure 1D:
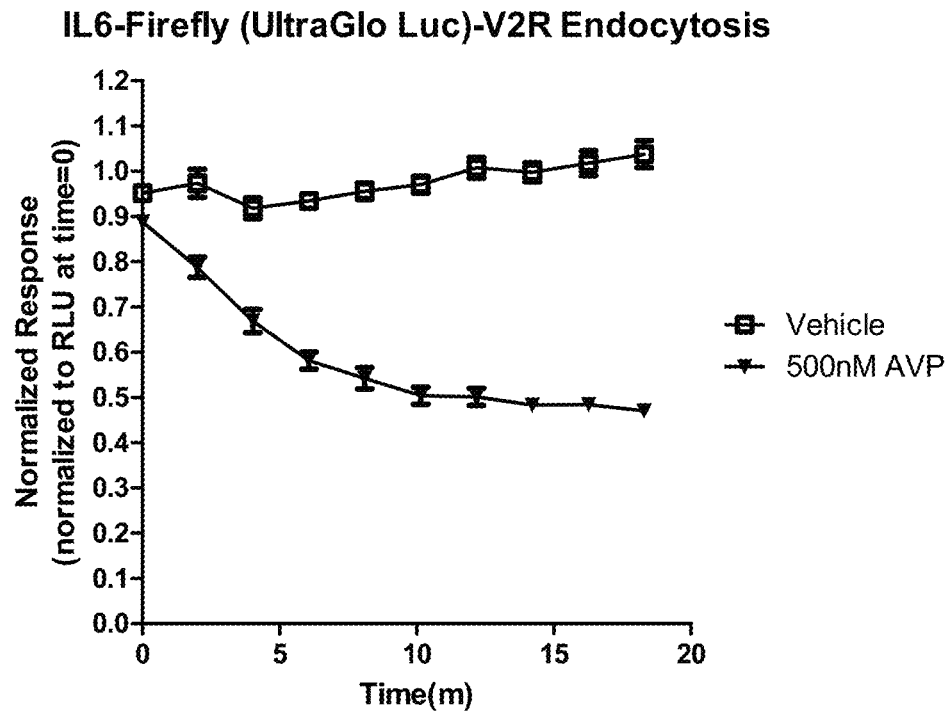

As used herein, the term "transmembrane trafficking" refers to the movement of an analyte, cell surface component, protein, etc. across a biological membrane or lipid bilayer, by any suitable mechanism. The term "transmembrane trafficking" applies to movement across the cell membrane, intracellular membranes, vesicular membranes, the nuclear membrane, an organelle membrane (e.g., chloroplast, mitochondria, endoplasmic reticulum, golgi complex, endosomes, vacuoles, etc.). The term "transmembrane trafficking" applies to movement across a membrane by any suitable mechanism (e.g., endocytosis, phagocytosis, autophagic flux, membrane translocation, exocytosis, autophagy, transmembrane movement, etc.).

As used herein, the terms "extracellular," "extracellular space," and "extracellular region" refer a physical space not contained within a cell, outside a cell, outside of a cell membrane, and/or not contained within a cell membrane. For example, the region immediately adjacent to a cell, but not within the plasma membrane is defined as being extracellular.

As used herein, the terms "intracellular," "intracellular space," and "intracellular region" refer a physical space contained within a cell and/or enveloped within a cell membrane. The "cytoplasmic," "nuclear," "endosomal," and other compartments or organelles within a cell are within the "intracellular space."

DETAILED DESCRIPTION

Provided herein are compositions and methods for monitoring the movement of analytes and/or cellular components across biological membranes (e.g., cell surface internalization). In particular, reporter constructs are provided, the transmembrane movement of which (e.g., by endocytosis), is monitored by methods described herein. Compositions and methods described herein are suitable for the detection and monitoring of various types of transmembrane trafficking. However, most embodiments described herein specifically focus on cell surface internalization and/or endocytosis. It should be noted that, in some embodiments, the compositions and methods described herein are suitable for detecting and/or monitoring other types of trafficking (e.g., phagocytosis, autophagic flux, membrane translocation, exocytosis) across other cellular membranes (e.g., intracellular membranes, vesicular membranes, the nuclear membrane, organelle membranes, etc.). Embodiments described herein are not limited to any one type of membrane trafficking or any one class of membranes. Embodiments herein that specifically address endocytosis should be viewed as more broadly applying to other type of transmembrane trafficking as well.

Provided herein are compositions and methods for monitoring cell-surface internalization and/or endocytosis by cells. In particular, reporter constructs (e.g., fusions of cell surface components and reporter proteins) are provided, the internalization of which (e.g., by endocytosis), is monitored by methods described herein. In some embodiments, compositions (e.g., cell surface component/reporter fusion proteins) and methods of use thereof, that provide a simple method to monitor endocytosis in real time, in living cells, and/or without the disadvantages of the existing methods are provided. In some embodiments, methods are performed on a solid support, e.g., microplate. In some embodiments, methods and compositions are provided for determining the amount, rate, duration, timing, triggers, and/or inhibitors of endocytosis of a cell surface component, e.g., cell surface receptor or protein. In some embodiments, the internalization assay methods described herein are minimally invasive, compatible with transiently transfected cells, and/or utilize a non-destructive endpoint for multiplex analysis of endocytosis with other functional assay endpoints, e.g., measurements of second messenger signaling, viability, cytotoxicity or similar phenotypic assays.

In some embodiments, compositions and methods for monitoring and/or detecting the internalization and/or endocytosis of cell surface proteins, e.g., a cell surface receptor, cell-surface analyte, etc. In some embodiments, a reporter element, e.g., a reporter protein (e.g., luciferase) that produces a detectable signal (e.g., through interaction with a substrate, via a detectable label, through an interaction with another molecule, etc.) is tethered to the cell surface in the non-cytoplasmic space (e.g., extracellular space, e.g., to a cell surface receptor). In some embodiments, internalization or endocytosis of the region of the cell membrane or the particular cell membrane component to which the reporter element is attached results in internalization or endocytosis of the reporter element. In some embodiments, a detectable change in the signal emitted (e.g., loss of signal, reduction in signal, change of frequency, increase in signal, gain of signal, change in wavelength, etc.) occurs upon internalization of the reporter molecule (e.g., through endocytosis). In some embodiments, monitoring the signal emitted (e.g., by endpoint detection, by real-time monitoring, etc.) provides a method of detecting internalization of the reporter element. In some embodiments, monitoring the signal emitted, and/or the internalization of the reporter molecule, provides methods for studying or monitoring endocytosis (e.g., rate, timing, duration, amount, etc.) and the affects of various intracellular conditions, extracellular conditions, molecular components, and pharmaceutical agents thereon. In some embodiments, compositions and methods for tethering a reporter element(s) to the cell surface, detecting the signal emitted (e.g., on the cell surface or within a cell or endosome), monitoring reporter signals (e.g., in real time, via endpoint detection, etc.), assessing the affects of conditional changes (e.g., introduction of drug-like molecules) on endocytosis, etc., are provided.

In some embodiments, a reporter protein, e.g., an enzyme (e.g., luciferase), is attached to a cell surface receptor, thereby tethering the reporter protein to the cell surface to monitor internalization and/or endocytosis of the cell surface receptor. In some embodiments, a reporter protein and cell surface receptor protein are expressed as a single fusion protein, e.g., from a fusion construct (e.g., genetic construct). In some embodiments, a reporter protein and cell surface receptor protein stably associate (e.g., covalently or non-covalently) to form a fusion. In some embodiments, a reporter protein and cell surface receptor protein are non-genetically coupled to form a fusion protein. In some embodiments, internalization, e.g., through endocytosis, of the cell surface receptor results in internalization of the reporter protein. In some embodiments, the signal from the reporter protein is altered upon endocytosis of the cell surface receptor (and reporter). In some embodiments, monitoring the signal from the reporter molecule over time provides a means for detecting internalization and/or endocytosis of the cell surface receptor (e.g., as the signal is altered upon internalization).

In some embodiments, a means of attaching, adhering, anchoring, associating, tethering, etc. a reporter element to the cell membrane, e.g., to monitor internalization of the reporter and adjacent cell membrane, is provided. In some embodiments, a cell surface component is utilized to attach, adhere, anchor, associate, tether, etc. a reporter element to the cell surface. In some embodiments, a fusion element comprising a reporter element and a cell surface component are provided. In some embodiments, the cell surface component is any element, e.g., protein, capable of attaching, adhering, anchoring, associating, tethering, etc. a fusion element to a cell surface. In some embodiments, the cell surface component comprises a protein, peptide, polypeptide, lipid, carbohydrate, viral particle, macromolecular complex, etc. In some embodiments, the cell surface component is a protein, peptide, or polypeptide. In some embodiments, the cell surface component is a membrane-associated protein, membrane-bound protein, cell surface receptor, transmembrane receptor, etc. In some embodiments, a receptor is an ion channel-linked receptor (e.g., acetylcholine receptor), enzyme-linked receptor (e.g., receptor tyrosine kinases; tyrosine kinase associated receptors; receptor-like tyrosine phosphatases; receptor serine/threonine kinases; receptor guanylyl cyclases, histidine kinase associated receptors), and/or G-protein-coupled receptor/7-transmembrane receptor. Particular transmembrane receptors that find use in embodiments described herein include, but are not limited to: angiotensin2-type1a receptor (AT1R), vasopressin 2 receptor (V2R), delta-opioid receptor (OPRD1) and epidermal growth factor receptor (EGFR) delta opioid receptor, vasopressin 2 receptor, EDG1 receptor, β2-adrenergic receptor (ADRB2), arginine vasopressin receptor 2 (AVPR2), serotonin receptor 1a (HTR1A), m2 muscarinic acetylcholine receptor (CHRM2), chemokine (C-C motif) receptor 5 (CCR5), dopamine D2 receptor (DRD2), kappa opioid receptor (OPRK), or α1a-adregenic receptor (ADRA1A), the insulin growth factor-1 receptor (IGF-R), etc. It is to be understood that the methods and compositions of the present invention are not limited to the cell surface components (e.g., cell membrane proteins) listed herein.

In some embodiments, reporter elements or complexes are provided that emit a detectable signal that is altered (e.g., reduced) upon cellular internalization and/or endocytosis of the reporter. In some embodiments, a fusion element comprising a cell surface component and a reporter element is provided. In some embodiments, the reporter element is any molecule, macromolecule (e.g., protein), or complex that produces a detectable signal, e.g., upon interaction with a substrate or upon stimulation (e.g., by change in pH, by exposure to light). In some embodiments, a reporter element is a protein. In some embodiments, a reporter element is an enzyme. In some embodiments, a reporter, a reporter substrate, and/or a reporter/substrate complex is detectable by optical, spectroscopic, photochemical, biochemical, immunological, chemical and/or magnetic means. In some embodiments, a reporter, a reporter substrate, and/or a reporter/substrate complex comprises a label. Suitable labels include, but are not limited to, colored, radioactive, fluorescent, ultraviolet, and/or magnetic molecules or particles. In some embodiments, a reporter, a reporter substrate, and/or a reporter/substrate complex is labeled by one or more of: antibodies, genetic probes, dyes, fluorochromes, proteins, peptides, amino acids, sugars, polynucleotides, enzymes, coenzymes, cofactors, antibiotics, steroids, hormones or vitamins. In some embodiments, a reporter, a reporter substrate, a reporter/substrate complex, and/or a label thereon generates a measurable signal which is detected with or without a stimulatory event. In some embodiments, a detectable substrate (e.g., fluorescent, radioactive, optically detectable, contrast agent, etc.) contacts, interacts, associates with, and/or binds a reporter. In some embodiments, the substrate of a reporter is detectable. In some embodiments, a reporter is detectable. In some embodiments, a reporter is a peptide, polypeptide, or protein. In some embodiments, reporter proteins include enzymes such as chloramphenicol acetyl transferase (CAT), β-glucuronidase (GUS) or β-galactosidase. In some embodiments, a reporter is luminescent, fluorescent, and/or chemiluminescent. In some embodiments, a reporter comprises proteins such as luciferases, beta lactamase, and alkaline phosphatase. In some embodiments, a reporter comprises a luciferase, e.g., a beetle luciferase, e.g., a firefly luciferase (e.g., *Photinus pyralis* or *Photuris pennsylvanica*), *Renilla* luciferase, *Gaussia* luciferase, *Oplophorus* luciferase, luciferin-utilizing luciferases, coelenterazine-utilizing luciferases, and any suitable variants or mutants thereof. In some embodiments, reporter proteins comprise enzymes capable of multiple substrate turnovers. In some embodiments, reporter proteins are not limited to traditional enzymes. In some embodiments, reporter proteins are wild-type proteins or mutated, e.g., thermostable and/or chemostable, forms which provide advantages over wild-type for use in reporter assays.

In some embodiments, a substrate, ligand, binding partner, label, etc. for a reporter element is provided. In some embodiments, any suitable interaction partner (e.g., substrate, ligand, antibody, label. etc.) for a reporter element is provided. In some embodiments, a reporter element is an enzyme, and an enzyme substrate is provided. In some embodiments, the enzyme substrate is coelenterazine, luciferin, \other suitable luciferase substrates or derivatives thereof In some embodiments, interaction of a reporter enzyme and enzyme substrate provides a detectable signal, e.g., luminescence, from the enzyme interacting with the enzyme substrate. In some embodiments, an interaction partner for a reporter element comprises a detectable label that is associated with the reporter upon interaction with the interaction partner. In some embodiments, a substrate, ligand, binding partner, etc. is membrane permeable. In some embodiments, a substrate, ligand, binding partner, etc. is capable or permeably passing through a cell membrane, endosomal membrane, vacuolar membrane, nuclear membrane, and/or other intracellular membrane. In some embodiments, a substrate, ligand, binding partner, etc. is membrane impermeable. In some embodiments, a substrate, ligand, binding partner, etc. is soluble in an intracellular, extracellular, and/or aqueous environment. In some embodiments, a substrate for a reporter element (e.g., enzyme) is provided. In some embodiments, a reporter element (e.g., enzyme) is capable of multiple substrate turnovers.

In some embodiments, the present invention provides fusion proteins comprising one or more reporter elements, e.g., reporter proteins or enzymes (e.g., luciferase) attached either directly, by a linker, or through another element, to a cell surface component or integral cell membrane protein. In some embodiments, a fusion protein comprises one or more additional peptide segments to provide functionality, e.g., cell export, secretion, or surface localization, or enhance the performance of the fusion protein. In some embodiments, a fusion protein comprises a secretion peptide, e.g., IL-6 signal peptide (e.g., SEQ ID NO. 1). In some embodiments, a fusion protein comprises an N-terminal secretion peptide, e.g., IL-6 signal peptide (e.g., SEQ ID NO. 1).

In some embodiments, a reporter element (e.g., reporter enzyme) coupled to a cell surface analyte (e.g., cell surface protein) is provided. In some embodiments, a reporter element and cell surface analyte are genetically expressed as a fusion. In some embodiments, a reporter element and cell surface analyte react (e.g., post-translationally) to form a fusion. In some embodiments, a reporter element and cell surface analyte are coupled, linked, and/or attached covalently or non-covalently. In some embodiments, the present invention provides fusion proteins comprising one or more reporter proteins, e.g., reporter enzyme (e.g., luciferase), covalently linked by a linker, e.g., GSSG linker (e.g., SEQ ID NO. 2), to a cell surface component or integral cell membrane protein. In some embodiments, a fusion protein comprises one or more additional peptide segments attached to the reporter protein and/or cell surface component or integral cell membrane protein via a linker, e.g., GSSG linker (e.g., SEQ ID NO. 2). In some embodiments, a linker is a peptide. In some embodiments, suitable linkers provide adequate spacing between elements without interfering with the structure and/or biological activity of the elements. In some embodiments, a linker is a non-peptide linker, e.g., polymer, alkyl chain, etc. In some embodiments, suitable linkers are understood in the art. The present invention is not limited by the sequence of a peptide linker sequence.

In some embodiments, a reporter element, e.g., a reporter protein or enzyme, is attached to the N-terminus, and/or an internal portion of a cell surface component, e.g., a cell surface receptor or other cell surface protein. In some embodiments, a reporter element, e.g., a reporter protein or enzyme, is attached to the N-terminus of a cell surface component, e.g., a cell surface receptor or other cell surface protein. In some embodiments, a reporter element is attached to a portion of cell surface component so as to not interfere with the overall structure and/or function of the cell surface component. In some embodiments, a cell surface receptor is attached to the N-terminus and/or an internal portion of a reporter element, e.g., a reporter protein or enzyme. In some embodiments, a reporter element is attached to portion of cell surface component so as to not interfere with the overall structure and/or function of the reporter element. In some embodiments, a reporter element is attached to the N-terminus of a cell surface receptor, e.g., GPCR, non-GPCR receptor (e.g., tyrosine kinase receptor, etc.).

In some embodiments, assays for the detection of endocytosis and reagents, e.g., fusion proteins, reporter elements, cell surface components (e.g., cell surface receptors), substrates, expression constructs, test reagents, etc., materials (e.g., microplates) and devices (e.g., luminometers) for execution thereof are provided. In some embodiments, the assays described herein exploit changes in the detectable signal emitted upon endocytosis. Experiments conducted during development of embodiments of the present invention using a variety of reporter elements demonstrated that the signal emitted is altered upon endocytosis of the reporter element. The present invention is not limited to any particular mechanism of altering the detectable signal of the reporter molecule. An understanding of the mechanism of action is not necessary to practice the present invention. In some embodiments, any reporter element, e.g., reporter protein or enzyme (e.g., luciferase)) that emits a signal that is detectably different when tethered to the surface of a cell (e.g. by attachment to a cell surface protein) and following endocytosis finds use in the embodiments herein. In some embodiments, the detectable change in the reporter signal upon endocytosis of the reporter element comprises: loss of signal, reduction of signal, enhancement of signal, gain of signal, alteration of signal (e.g., change in wavelength emitted, etc.), etc. In some embodiments, the change in signal is due to the endocytic environment (e.g. pH, salt concentration, steric constraint, etc.), degradation of the reporter element, recycling of reporter element to the cell surface, loss of substrate availability, or any other mechanism that results in a detectably different signal upon endocytosis of the reporter element. The present invention is not limited to any particular mechanism of altering the detectable signal of the reporter molecule, and an understanding of the mechanism of action is not necessary to practice the present invention.

In some embodiments, real-time (e.g., rapid/repeated detection throughout a time course) detection and/or monitoring of endocytosis is provided. In some embodiments, end-point (e.g., detection and/or monitoring of endocytosis is provided. In some embodiments, end-point (e.g., detection and/or monitoring of endocytosis is compared to a control or standard to identify the presence, absence, rate, amount, etc. of endocytosis. In some embodiments, detection and/or monitoring are performed at one or more time points (e.g., time=0 s, 1 s, 2 s, 5 s, 10 s, 30 s, 1 min, 2 min, 5 min, 10 min, 15 min, 30 min, 1 hour, 2 hours, 5 hours, or any suitable time points therein). In some embodiments, the reporter signal is detected prior to addition of substrate. In some embodiments, the reporter signal is detected upon addition of substrate (e.g., time=0). In some embodiments, the reporter signal is detected following addition of substrate. In some embodiments, the reporter substrate is added to cells prior to triggering of endocytosis. In some embodiments, the reporter substrate is added to cells after triggering of endocytosis. In some embodiments, the reporter substrate is added to cells prior to allowing endocytosis to occur. In some embodiments, the reporter substrate is added to cells after allowing endocytosis to occur. In some embodiments, the reporter signal and/or reporter/substrate signal is detected prior to endocytosis, e.g., to establish background, baseline, or pre-endocytosis level signal). In some embodiments, time is allowed for endocytosis to occur. In some embodiments, endocytosis is triggered by any suitable method, e.g., receptor agonists (e.g., small molecule, cytokines, etc.), modified growth conditions, pharmacologic compounds, changes in cellular signaling pathways, presence of any endocytosis inducing species, etc. In some embodiments, a biological process that is known to lead to endocytosis is induced by any suitable method. In some embodiments, the reporter signal and/or reporter/substrate signal is continuously or periodically (e.g., intervals of: 1 s, 2 s, 5 s, 10 s, 30 s, 1 m, 2 m, 5, 10 m, etc.) monitored following initial detection. In some embodiments, the reporter signal and/or reporter/substrate signal is continuously or periodically monitored following addition of the reporter substrate. In some embodiments, the reporter signal and/or reporter/substrate signal is continuously or periodically monitored following triggering of endocytosis, e.g., by addition of a receptor agonist. In some embodiments, real-time monitoring of endocytosis is provided by detecting the reporter signal over time, e.g., at closely spaced intervals (e.g., 1 s, 2 s, 5 s, 10 s, 30 s, 1 m, 2 m, etc. In some embodiments, detection of endocytosis is provided by detecting the reporter signal at one or more fixed time points, e.g., 15 min, 20 min, 30 min., etc. In some embodiments, measurement of the rate, amount, duration, etc. are provided by real-time assays. In some embodiments, measurement of endocytosis is provided by detecting the reporter signal after stimulation of endocytosis via endpoint.

In some embodiments herein, compositions and methods for monitoring, detecting, or quantitating endocytosis are provided. In some embodiments, compositions and methods described herein are useful for monitoring any type of endocytosis, e.g., clathrin-mediated, caveole, macropinocytosis, or phagocytosis. In some embodiments, endocytosis is monitored irrespective of the endocytosis pathway and/or endocytic components involved in the process. In some embodiments, compositions and methods are configured to detect all types of endocytosis. In some embodiments, compositions and methods to detect dynamin-dependent endocytosis are provided. In some embodiments, compositions and methods are provided to detect one or more types endocytosis, e.g., clathrin-mediated, caveole, macropinocytosis, phagocytosis, and/or dynamin-dependent. In some embodiments, compositions and methods are provided to detect a single type of endocytosis, e.g., clathrin-mediated, caveole, macropinocytosis, dynamin-dependent, or phagocytosis.

In some embodiments, nucleic acid constructs and vectors are provided that encode and/or are capable of expressing one or more protein components (e.g., reporter, receptor, fusion, etc.) of the methods and assays described herein. In some embodiments, vectors and/or constructs comprise sequences and regulatory elements that allow the encoded proteins to be expressed by the cellular transcription and translation machinery. In some embodiments, vectors and/or constructs comprise one or more of enhancer regions, promoter regions, start codons, termination codons, transcription termination sequences, portable translation initiation sequences, gene coding regions, gene insertion regions, etc. In some embodiments, constructs are provided that provide a cloning site for inserting a nucleic acid encoding a cell surface receptor, or other cell surface protein, for fusion with a reporter element. In some embodiments, vectors are provided for stable or transient expression of reporter elements and/or fusion proteins in cells. In some embodiments, suitable vectors, delivery systems (e.g., viral gene delivery), plasmids, (e.g., pF5A plasmid and plasmids derived there from, etc.), and constructs are provided for producing the protein compositions and performing the methods described herein are provided.

In some embodiments, kits containing components, reagents, e.g., fusion constructs, reporter proteins, substrates, etc., and/or materials (e.g., multiwell plates, cells) are provided. In some embodiments, kits are provided for performing the methods or assays described herein. In some embodiments, materials and reagents are provided in kits to produce, express, and/or engineer constructs, fusion proteins, etc. for carrying out methods of the present invention.

In some embodiments, methods and assays that are performed in a multiplex format are provided. In some embodiments, methods and assays are performed in a high throughput manner, e.g., to screen inhibitors or enhancers of endocytosis. In some embodiments, assays provided herein are rapidly performed in a multiwell plate, e.g., 96-well, 384-well, etc. In some embodiments, assays measure endocytosis in high-throughput screening compatible, mix and read format (e.g., non-image based, flow-based, etc.).

In some embodiments, systems, devices, or apparatuses for assessing, quantitating, detecting, and/or monitoring the compositions, methods, and/or assays are provided. In some embodiments, systems, devices, and/or apparatuses are provided to detect, quantitate, or monitor, the amount of a reporter element on the exterior of a cell, the amount of reporter element endocytosed, and/or the endocytosis of reporter element. In some embodiments, detection, quantification, and/or monitoring are provided by a device, system or apparatus comprising one or more of a spectrophotometer, fluorometer, luminometer, photomultiplier tube, photodiode, nephlometer, photon counter, electrodes, ammeter, scintillation counter, Geiger counter, voltmeter, capacitative sensors, radio-frequency transmitter, magnetoresistometer, flow cytometer, CCD, Hall-effect device, etc. In some embodiments, a device suitable for detection of a given reporter element, e.g., luciferase, beta lactamase, or radiolabel, is selected and/or provided. In some embodiments, assays, methods, and compositions that are compatible detection systems that are comparatively inexpensive, e.g., low-moderate price luminometer as opposed to high-end fluorometer, are provided.

In some embodiments, methods to study or analyze endocytosis, and the role of intracellular or extracellular processes, components (e.g., clathrin, dynamin, etc.), and other factors (e.g., cell type, cell stress, extracellular environment, etc.) on receptor internalization and/or endocytosis, are provided. In some embodiments, assays are provided for monitoring the effect of various factors on the rate, amount, duration, and/or timing of receptor internalization and/or endocytosis. In some embodiments, assays are provided for monitoring the effect of specific molecules, e.g., cellular components (e.g., clathrin, dynamin, etc.), drugs, etc., on the rate, amount, duration, and/or timing of receptor internalization and/or endocytosis. In some embodiments, assays are provided (e.g., high throughput, multiplex, etc.) for screening compounds for a desired effect on internalization and/or endocytosis of a specific receptor. In some embodiments, assays are provided for screening compounds to treat or prevent one or more conditions, diseases, or disorders that involve endocytosis, receptor internalization, or malfunction of a cell surface receptor. In some embodiments, assays are provided for identifying molecules that trigger, enhance, inhibit, or otherwise affect the rate, amount, duration, and/or timing of the internalization of a specific receptor or endocytosis in general.

EXPERIMENTAL

Example 1

Firefly Luciferase-Receptor Fusions and Cell-Permeable Substrates to Monitor Agonist-Induced Receptor Endocytosis Experiments were conducted during development of embodiments of the present invention to provide kinetic or endpoint measurements of endocytosis. The G-protein coupled receptors (GPCRs): angiotensin2-type1a receptor (AT1R), beta2-adrenergic receptor (B2AR), vasopressin 2 receptor (V2R), delta-opioid receptor (OPRD1) and epidermal growth factor receptor (EGFR) were fused to firefly luciferases, cloned into the pF5a vector (Promega Corp) and expressed in HEK293 cells. To achieve efficient cell surface expression of the luciferase reporter, the FFluc-GPCR fusion proteins further encoded N-terminal IL-6 secretion peptides. HEK293 cells were transfected with plasmid DNA encoding the FFluc-GPCR fusions using Fugene HD (Promega Corp.) according to the manufacturer's instructions. To achieve proper expression levels, 1 part plasmid DNA (by mass) was diluted into 100 parts carrier DNA (pGEM-3Z; Promega Corp.) yielding approximately 0.5 ng/well reporter DNA. For FFluc-V2R and FFluc-AT1R, plasmid DNA was transfected at 5 ng/well and 0.16 ng/well respectively. For transfection into HeLa cells, plasmid DNA was diluted 1:10 into carrier DNA yielding 5 ng/well plasmid DNA. Following transfection and 24 hour incubation at 37° C., the cell media was replaced with serum free medium (100 µL Opti-MEM; Invitrogen), and the cells serum starved for either 4 hours (for GPCR studies) or 24 hours (for EGFR studies). 50 µL per well of luciferase substrate, D-luciferin, was then added to a final concentration of 0.2 mM D-luciferin, 2 mM $MgCl_2$, and 2 mM ATP, and the cells incubated for 30 minutes at 37° C. For AT1R and V2R, 0.02 mM D-luciferin was used. For the luc2-B2AR experiment, 0.01 mM D-luciferin was used. For the FFLuc experiment using the D-luciferin derivative, PBI-3102, 0.02 mM substrate was used. Immediately prior to stimulation, luminescence was measured on a GLOMAX Multi Plus plate reader set to 0.5 s of integration time. Cells were then stimulated with the agonist indicated below (1/10 volume addition), and luminescence measured every two minutes in real-time. To achieve maximum levels of receptor internalization, the following concentrations of agonist were used for each receptor: 10 uM isoproterenol (ISO) for B2AR, 1 uM arginine vasopressin (AVP) for V2R, 500 nM angiotensin 2 (Ang2) for AT1R, or 10 uM SNC-80 for OPRD1. As controls, cells were treated with vehicle (Opti-MEM containing either DMSO or water). Normalized luminescence was determined by dividing the luminescence value (RLUs) of each sample by the luminescence from the same sample prior to stimulation (SEE FIG. 1A-D).

Figure 2A:
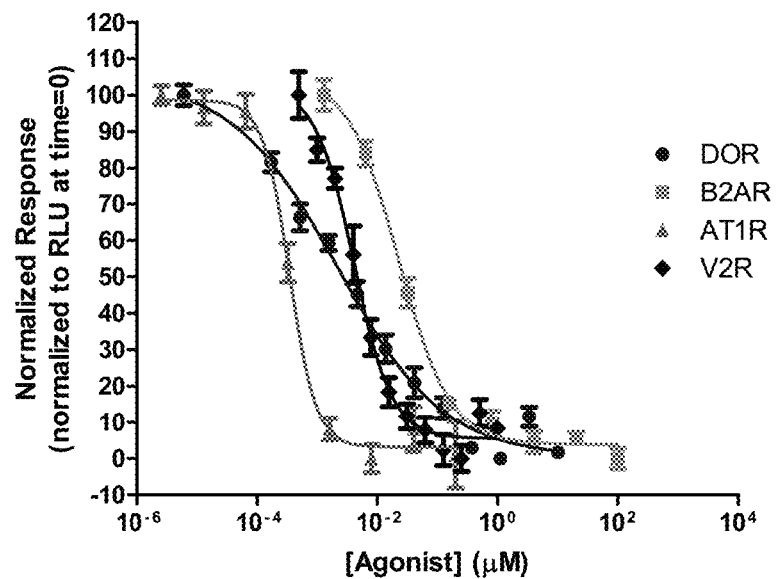
FIGS. 2A-F show fixed time-point concentration response curves: (A) Normalized concentration-response curves for 4 different GPCRs using a thermostable firefly luciferase (FFluc). The luminescence from each sample (agonist concentration) at 20 minutes was normalized to the luminescence of the same sample prior to stimulation; (B) EGF concentration response curve for endocytosis of EGFR/FFluc fusions; (C) Isoproterenol concentration response curve for endocytosis of FFLuc/B2AR fusion in HeLa cells; (D) Isoproterenol concentration response curve for endocytosis of an alternate variant of FFLuc (luc2) fusion to B2AR; (E) Isoproterenol concentration response curves for endocytosis of FFLuc/B2AR fusion using an alternate luciferin substrate based upon the D-luciferin structure (PBI-3102). (F) "Gain of signal" arginine vasopressin concentration response curve for endocytosis of FFLuc/V2R fusion by relying upon intracellular stores of Mg/ATP for luciferase activity.
Figure 2B:
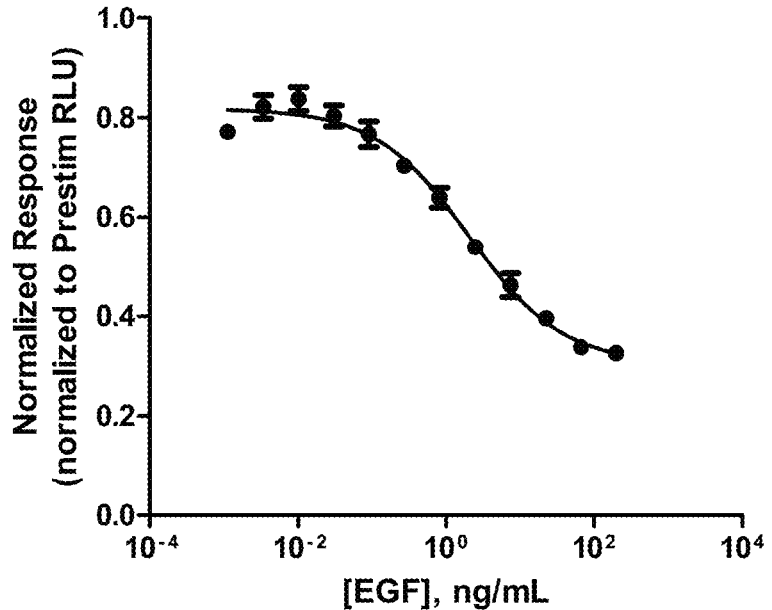
Figure 2C:
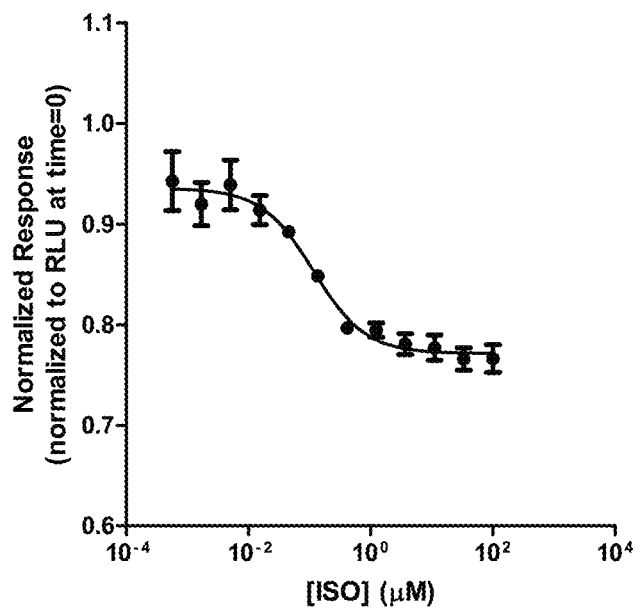
Figure 2D:
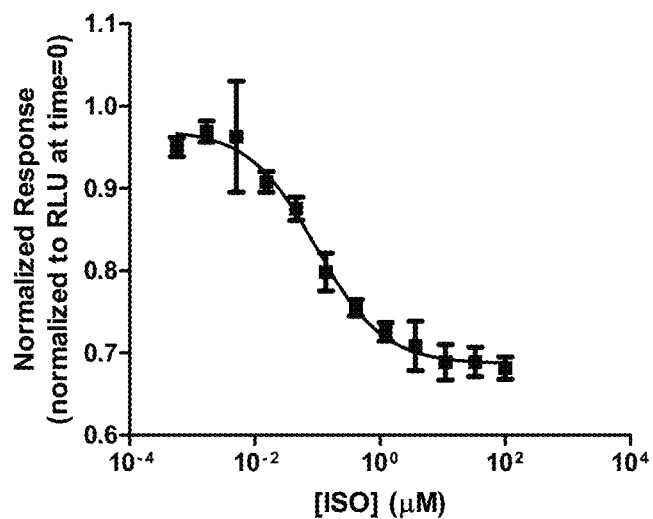
Figure 2E:
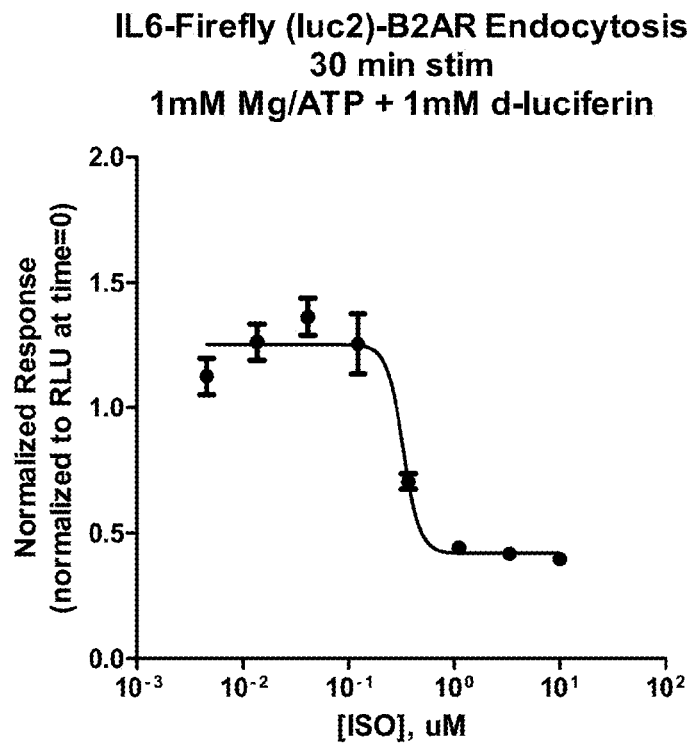

For GPCR concentration-response curves, the luminescence from each sample (agonist concentration) at 20 minutes was normalized to the luminescence of the same sample prior to stimulation (SEE FIG. 2A). These data were normalized to percent activation (lowest values assigned 0% and highest values assigned 100%). To determine if endocytosis of receptor tyrosine kinase could be measured using luciferase fusions, a FFLuc-epidermal growth factor receptor (EGFR) fusion was tested in the configuration as described above (FIG. 2B). The CRC of epidermal growth factor receptor (EGFR) endocytosis upon treatment with varying concentrations of epidermal growth factor (EGF) was determined from the luminescence of each sample (agonist concentration) at 2 hours normalized to the luminescence value of the same sample prior to stimulation (SEE FIG. 2B). The isoproterenol concentration response curves (CRC) of beta2-adrenergic receptor endocytosis in HeLa cells was determined from the luminescence of each sample (agonist concentration) at 20 minutes normalized to the luminescence of the same sample prior to stimulation (SEE FIG. 2C). The isoproterenol concentration response curves (CRC) of beta2-adrenergic receptor endocytosis using a D-luciferin derivative PBI3102 was determined from the luminescence of each sample (agonist concentration) at 20 minutes normalized to the luminescence of the same sample prior to stimulation (SEE FIG. 2D). The isoproterenol concentration response curves (CRC) of beta2-adrenergic receptor endocytosis using the FFLuc variant, luc2, was determined from the luminescence of each sample (agonist concentration) at 30 minutes normalized to the luminescence of the same sample prior to stimulation (SEE FIG. 2E).

Example 2

Figure 3:
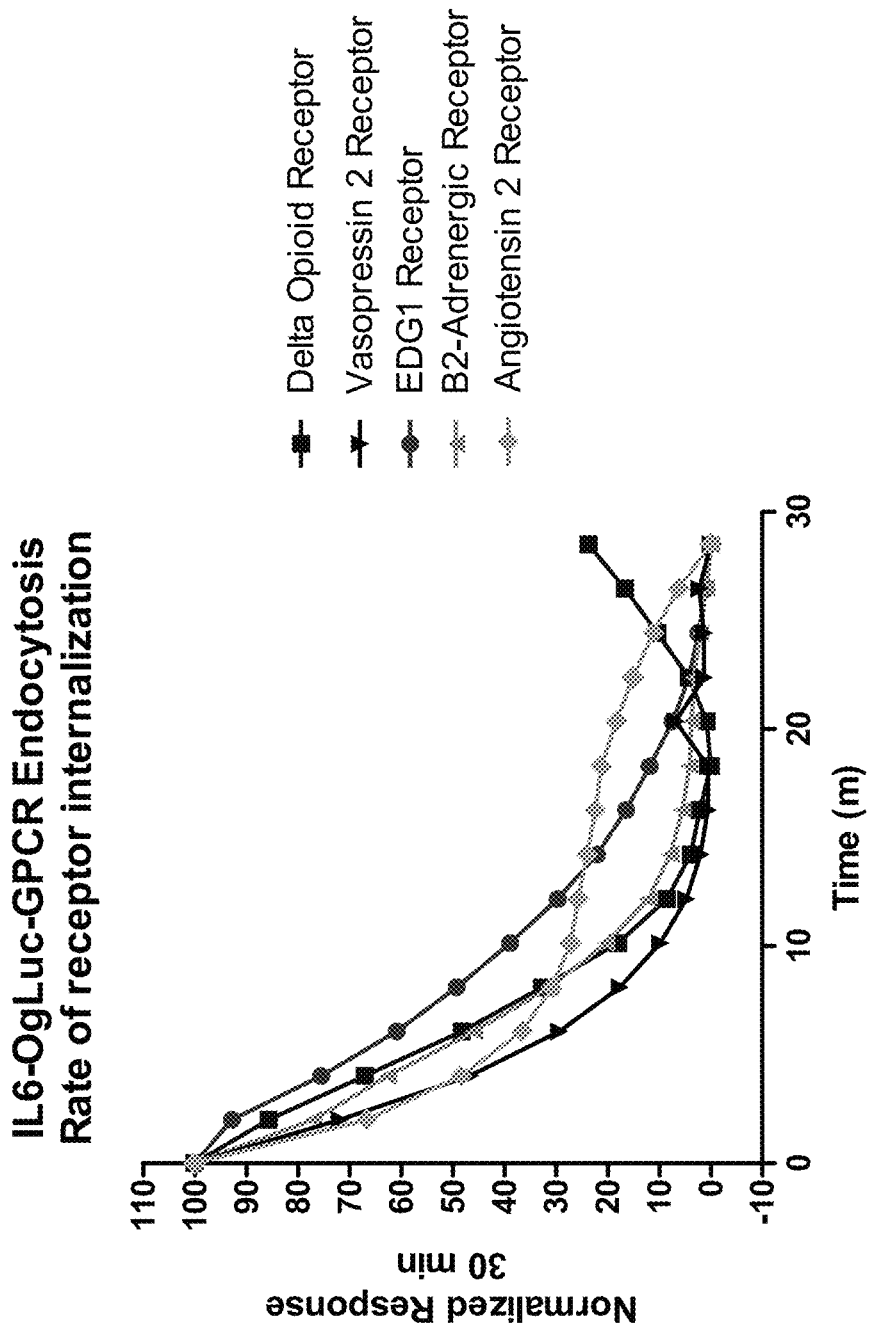
FIG. 3 shows single dose, normalized kinetic responses for endocytosis of various OgLuc/GPCR fusions in real time.

*Oplophorus* Luc-Receptor Fusions and Cell-Permeable Substrates to Monitor Agonist-Induced Receptor Endocytosis Experiments were conducted during development of embodiments of the present invention to investigate endocytosis of fusions of the five GPCRs described in Example 1 with two *Oplophorus* Luciferase (OgLuc) variants, 9B8 OgLuc and L27V OgLuc. HEK293 cells were transfected with plasmid DNA encoding OgLuc-receptor fusion using Fugene HD according to the manufacturer's instructions. To achieve proper expression levels, 1 part plasmid DNA was diluted into 1000 parts carrier DNA (pGEM-3Z) to yield 50 pg/well plasmid DNA. Following a 24 hour incubation, the cell media was replaced with serum free medium (100 µL of Opti-MEM), and the cells serum starved for 4 hours. 50 µL per well of a solution of PBI-3939 (a coelenterazine derivative; SEE FIG. 9) was then added to a final concentration of 20 µM, followed by incubation for 5 minutes at 37° C. Immediately prior to stimulation, luminescence was measured on a GLOMAX Multi Plus plate reader set to 0.5 s of integration time. Cells were then stimulated with the agonist indicated as described in Example 1, and luminescence measured every two minutes in real-time. Normalized luminescence was plotted versus time to observe the rates of internalization for the various fusion proteins (SEE FIG. 3).

Figure 4:
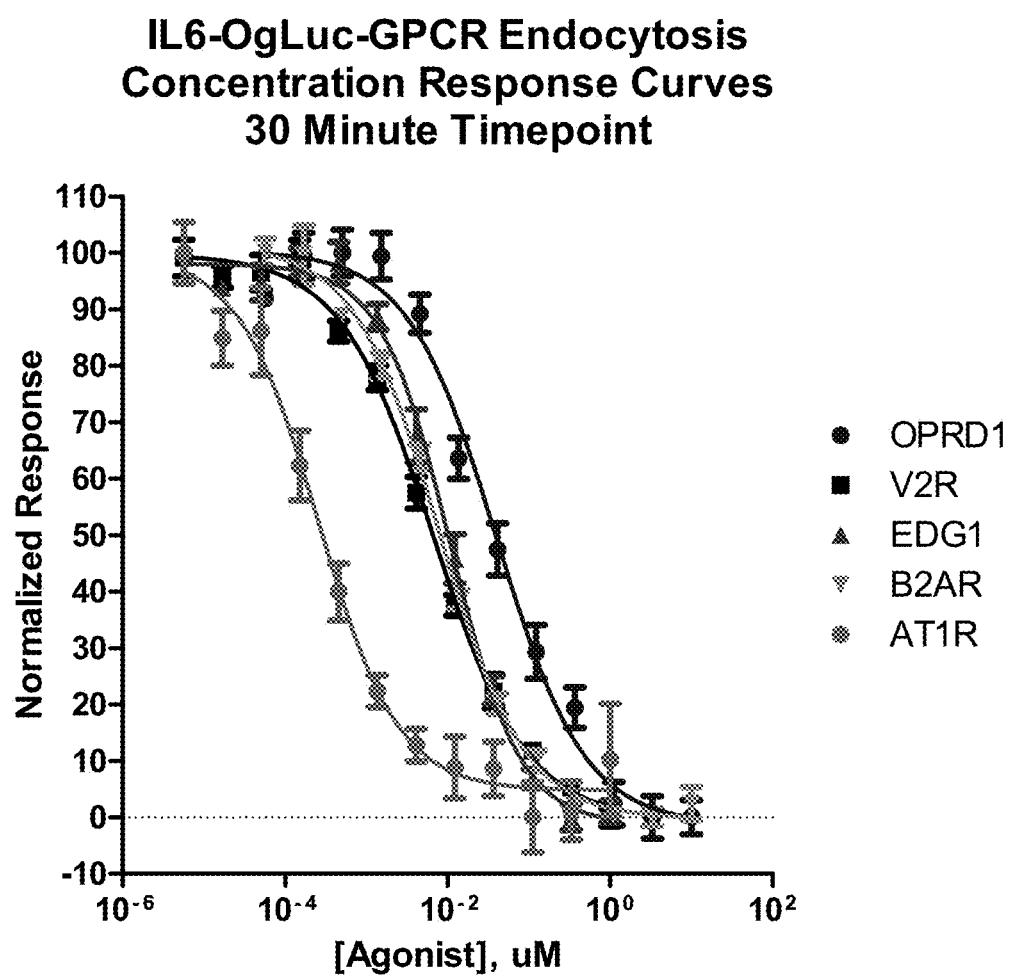
FIG. 4 shows normalized GPCR concentration-response curves for endocytosis of various OgLuc/GPCR fusions. Here, luminescence at 30 minutes was normalized to the luminescence of the same sample prior to stimulation. The normalized luminescence was plotted against agonist concentration FIGS. 5A-F (A-B) show graphs demonstrating agonist specificity of endocytosis induction of B2AR and V2R using OgLuc reporter proteins using methods as described above; (C-D) shows concentration response curves for endocytosis of OgLuc B2AR fusions using alternate coelenterazine derivatives as substrates (PBI-4525 and PBI-4377) as described above; (E-F) demonstrates the ability to measure endocytosis of OgLuc-B2AR or OgLuc-V2R by adding luciferase substrate after endocytosis has occurred (nonkinetic, endpoint measurement).

OgLuc GPCR fusions also enable measurement of agonist dose-responses (FIG. 4). Similar to FFLuc endocytosis, OgLuc-GPCR endocytosis was induced with varying concentrations of agonist (including sphingosine-1-phosphate (S1P) for EDG1). Normalized luminescence was determined by dividing the luminescence value of each sample by the luminescence from the same sample prior to stimulation. For CRC of various GPCRs, the normalized luminescence at 30 minutes stimulation was used. Data were then normalized to percent activation (lowest values assigned 0% and highest values assigned 100%)(SEE FIG. 4).

Figure 5A:
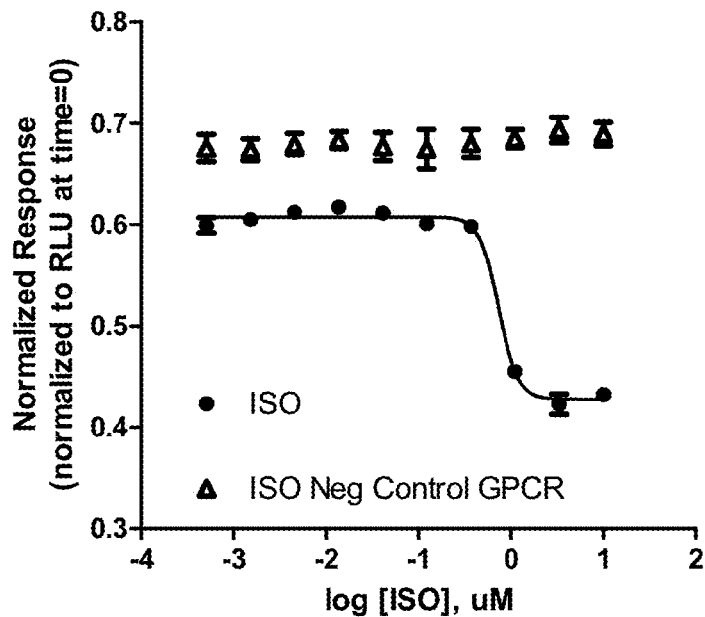
Figure 5B:
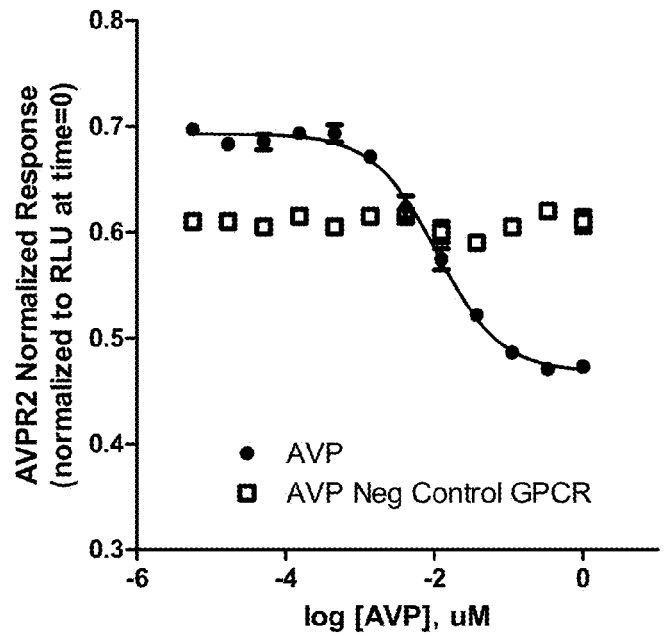

To determine the specificity of assay response, HEK293 cells were transfected with OgLuc-B2AR or OgLuc-V2R fusion proteins and treated as described above (FIG. 5 A-B). Known B2AR receptor agonists do not promote endocytosis of OgLuc-V2R fusion proteins (SEE FIG. 5B). Conversely, known V2R agonists do not promote endocytosis of OgLuc-B2AR fusion proteins (SEE FIG. 5A).

Figure 5C:
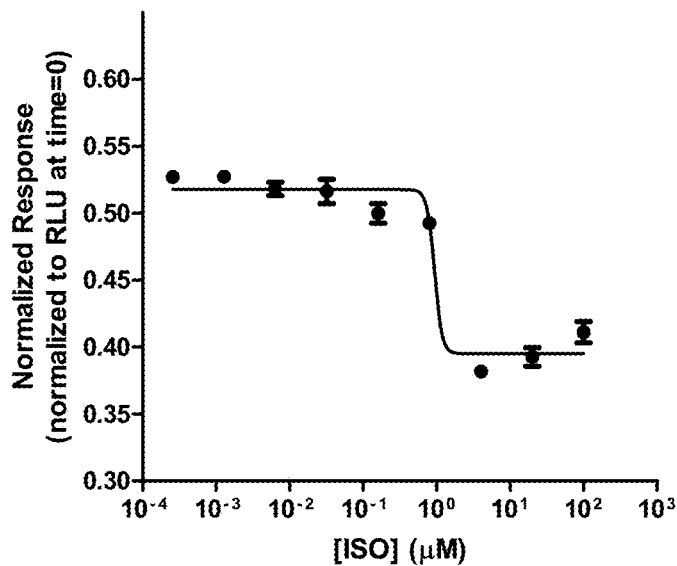
Figure 5D:
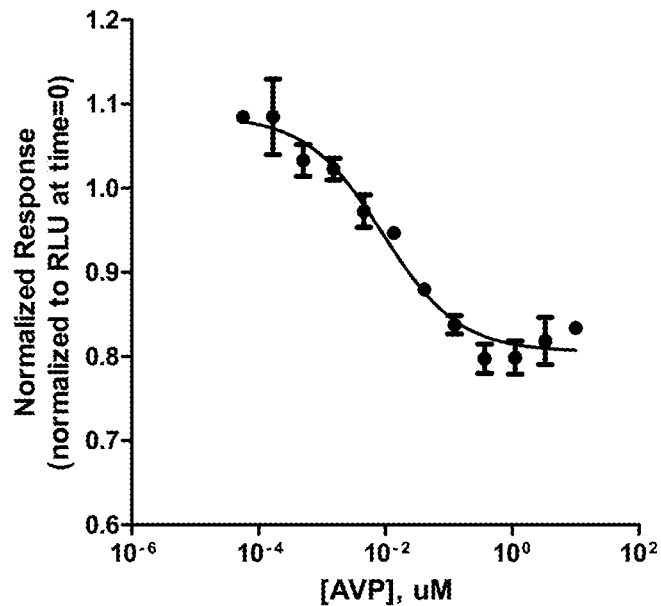
Figure 5E:
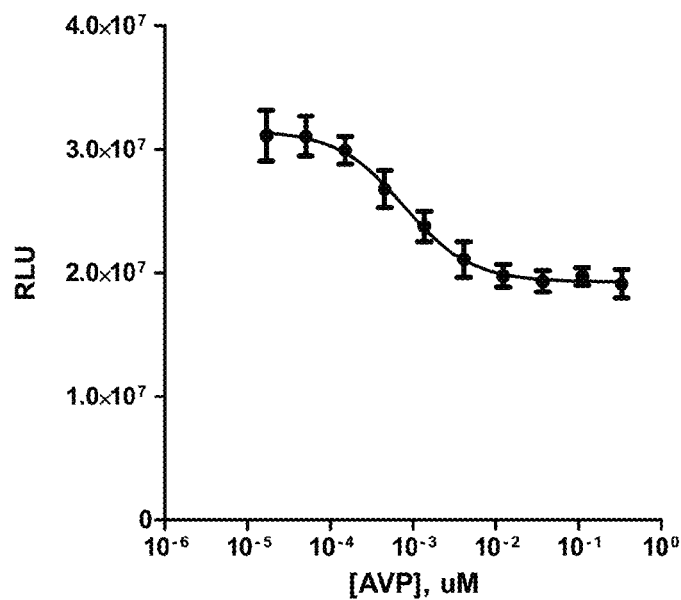
Figure 5F:
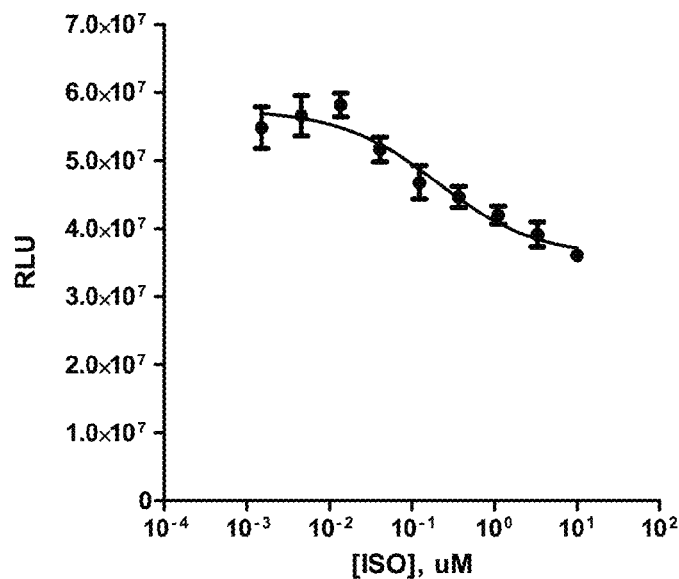

To determine whether coelenterazine substrates other than PBI-3939 would enable endocytosis measurements using OgLuc receptor fusions, the coelenterazine derivatives, PBI-4525 and PBI-4377 (SEE FIG. 9), were used to measure endocytosis of OgLuc(9B8)-B2AR (FIG. 5C-D). To achieve steady-state luciferase activity in the presence of PBI-4377 or PBI-4525, cells were pre-incubated with the substrate for 2 hours or 5 minutes, respectively, at 37° C. prior to stimulation. Luminescence measurements and data processing were conducted as described above.

To determine whether endocytosis measurements could be performed by adding substrate after stimulation of endocytosis, cells expressing OgLuc-B2AR (FIG. 5F) or OgLuc V2R (FIG. 5E) fusions as described above were stimulated as described above, but in the absence of luciferase substrate. After 30 minutes of incubation, PBI-3939 was added to a final concentration of 20uM, and luminescence was immediately measured via endpoint analysis. Raw luminescence values are plotted on the y-axis.

Example 3

Figure 6:
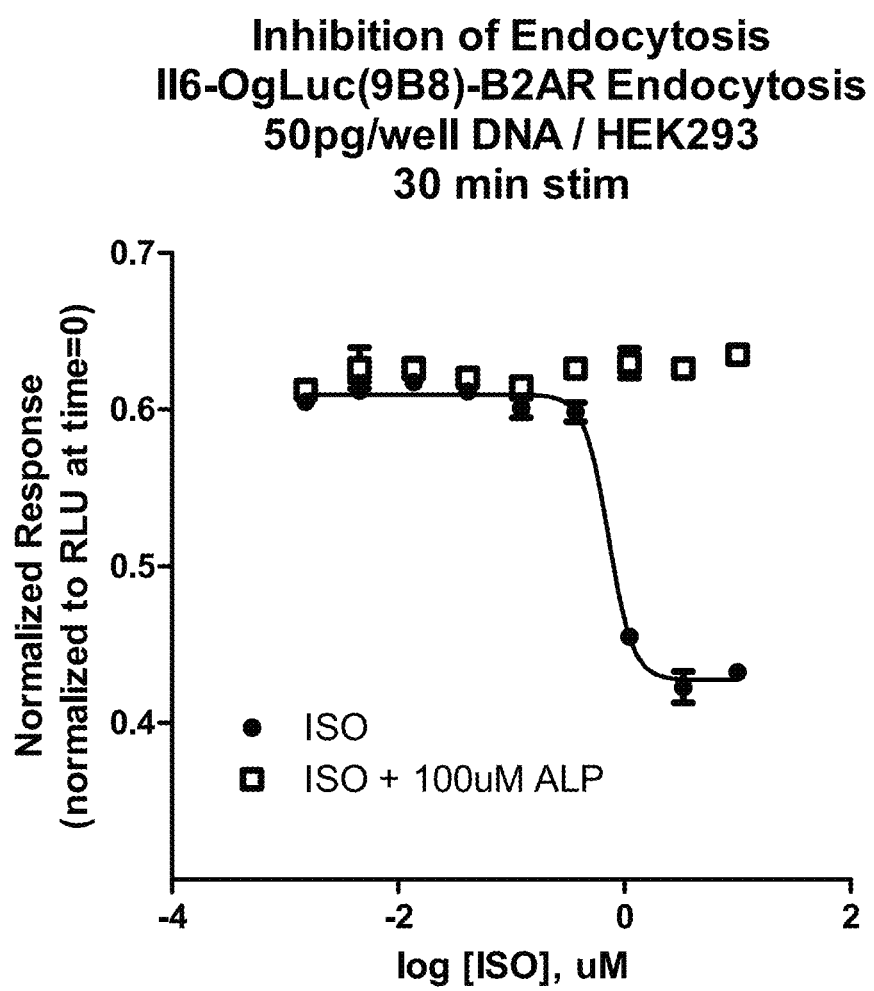
FIG. 6 shows an isoproterenol concentration response curve for OgLuc/B2AR endocytosis in the presence or absence of a B2AR endocytosis antagonist, alperenerol.
Figure 7:
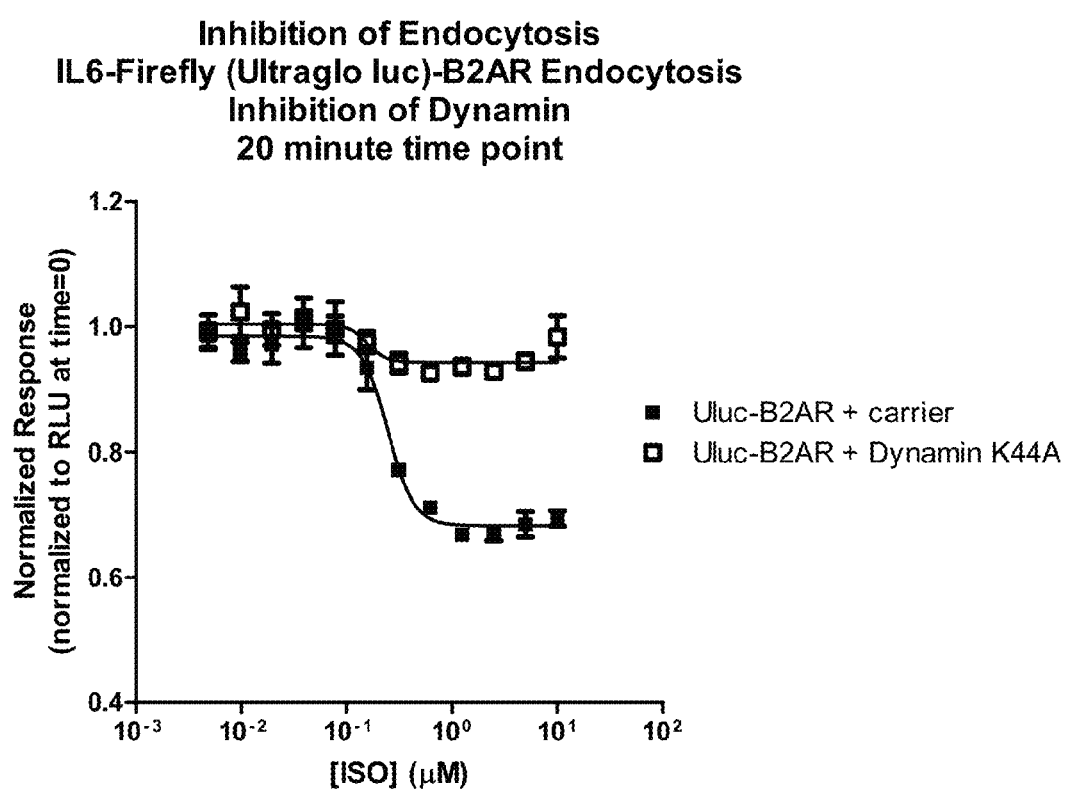
FIG. 7 shows a concentration response curve for FFLuc/B2AR endocytosis in the presence of co-expressed dominant-negative dynamin, demonstrating dependence on functional dynamin proteins for this assay readout

Luciferase-Receptor Fusions and Cell-Permeable Substrates to Monitor Inhibition of Receptor Endocytosis Experiments were conducted during development of embodiments of the present invention to detect inhibition of receptor endocytosis. CRCs of isoproterenol-induced endocytosis of OgLuc-B2AR fusions was performed as described in Example 2 except in the presence/absence of 100 µM alprenerol antagonist (added 15 minutes prior to treatment with isoproterenol) (SEE FIG. 6). CRCs of isoproterenol-induced endocytosis of FFluc-B2AR fusions was performed as described in Example 1 except in cells overexpressing dominant-negative dynamin (K44A). To co-express dynamin (K44A) and the FFluc-B2AR, the carrier DNA was replaced with plasmid DNA encoding dynamin (K44A) under control of a CMV promoter (SEE FIG. 7).

Example 4

Reduction of Luciferase Signal

Figure 8:
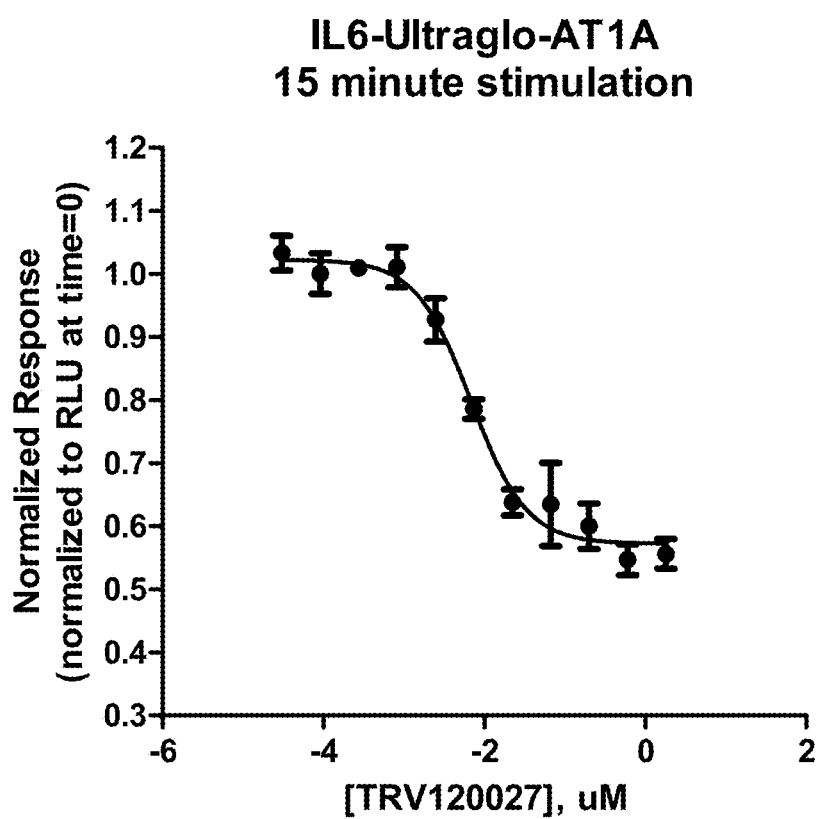
FIG. 8 shows a graph demonstrating G-protein independent signaling events using known β-arrestin-biased agonist TRV120027 with angiotensin-type1A receptor/firefly luciferase fusions.
Figure 9A:
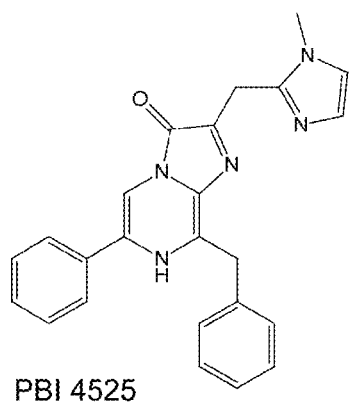
FIGS. 9A and 9B show the chemical structures of examples of luciferase substrates.
Figure 9A:
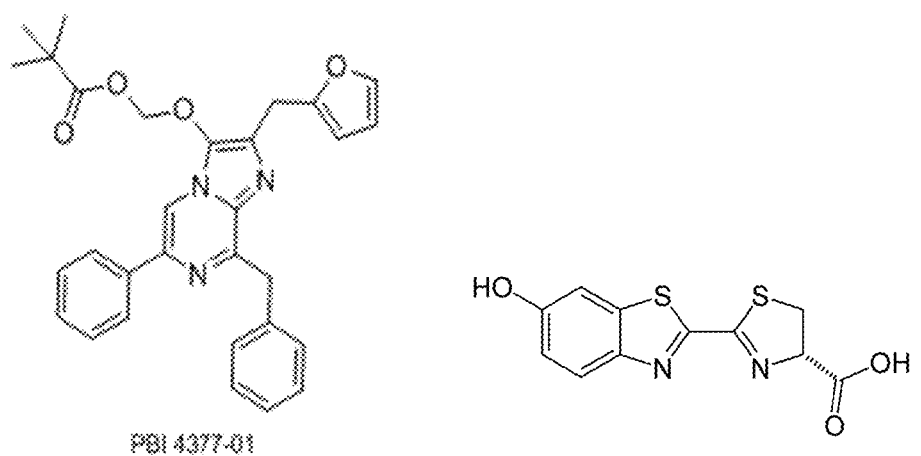
Figure 9A:
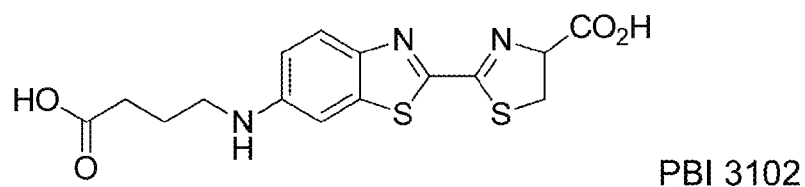
Figure 9B:
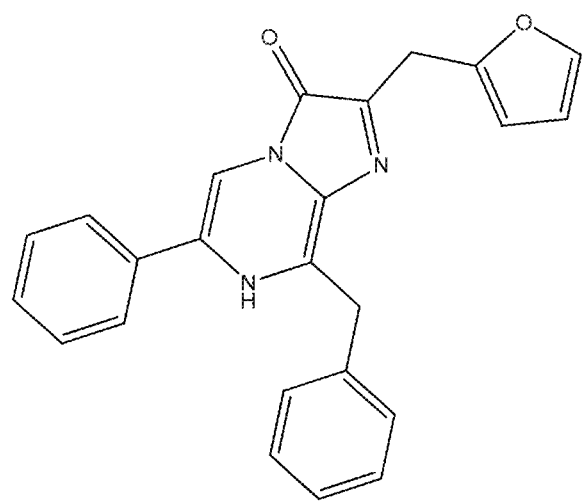

Experiments were conducted during development of embodiments of the present invention to investigate endocytosis of an AT1R/FFluc fusion in response to TRV120027, an agonist that does not promote G-protein activation (a.k.a β-arrestin-biased agonist). Cells were transfected with plasmid DNA encoding AT1R/FFluc fusion. Luciferin substrate was added, and the cells incubated as previously described Immediately prior to stimulation, luminescence was measured. Cells were then stimulated with varying concentrations of TRV 120027 for 15 minutes, and luminescence detected. Normalized luminescence was plotted versus agonist concentration to observe the internalization of the fusion proteins (SEE FIG. 8). These data demonstrate the independence of internalization on second messenger response. The assays detected internalization despite the agonist's inability to generate second messenger response as commonly measured in other assay formats (SEE FIG. 8).

Example 5

Receptor Recycling

Experiments described herein provide techniques and methods to detect and/or measure receptor recycling, e.g., endocytosis and exocytosis. For instance, receptor recycling could be measured by pulse-chase experiments in which, after inducing reporter endocytosis, the inducing agonist is removed. An increase in luminescence would indicate recycling/exocytosis of receptors to the cell surface.

Example 6

Increase in Luciferase Signal

Figure 2F:
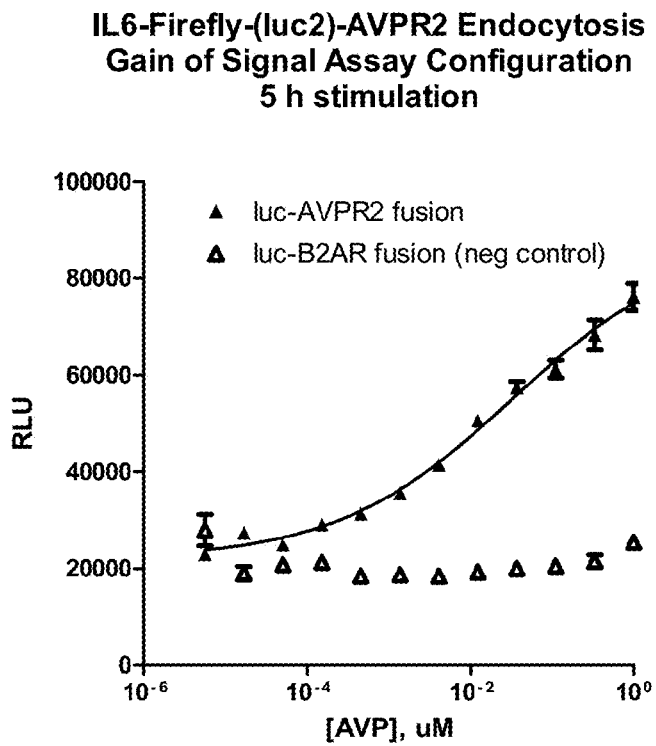

Experiments were conducted during development of embodiments of the present invention to provide endpoint measurements of endocytosis. The G-protein coupled receptor (GPCR) vasopressin 2 receptor (V2R) or negative control beta2-adrenergic receptor (B2AR) were fused to firefly luciferase (luc2), cloned into the pF5a vector (Promega Corp) and expressed in HEK293 cells. To achieve efficient cell surface expression of the luciferase reporter, the FFluc-GPCR fusion proteins further encoded N-terminal IL-6 secretion peptides. HEK293 cells were transfected with plasmid DNA encoding the FFluc-GPCR fusions using Fugene HD (Promega Corp.) according to the manufacturer's instructions. To achieve proper expression levels, 1 part plasmid DNA (by mass) was diluted into 100 parts carrier DNA (pGEM-3Z; Promega Corp.) yielding approximately 0.5 ng/well reporter DNA. Following a 24 hour incubation at 37° C., the cell media was replaced with serum free medium (100 µL Opti-MEM; Invitrogen), and the cells serum starved for 1 hour. After serum starvation, cells were stimulated with serially diluted arginine vasopressin (AVP) for 30 minutes. Extracellular luciferase was then inhibited via addition of a solution (50 µL/well) of trypsin/EDTA (Gibco) to a final concentration of 0.08% trypsin. Cells were incubated 30 minutes at 37° C. 50 µL/well of a solution of D-luciferin (without Mg/ATP) was then added (to a final concentration of 2 mM) and cells were incubated an additional 5 hours. Dose-dependent increase in raw luminescence signal is observed for V2R fusion proteins, whereas no increase is observed for negative control (B2AR) fusion proteins (See FIG. 2F).

All publications and patents provided herein are incorporated by reference in their entireties. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

SEQUENCES

SEQ ID NO. 1-IL6 signal peptide
ATGAACTCCTTCTCCACAAGCGCCTTCGGTCCAGTTGCCTTCTCCCTGGGGCTGCTCCTGGTGTTGCC
TGCTGCCTTCCCTGCCCCA SEQ ID NO. 2-GSSG Linker
GGCTCGAGCGGA SEQ ID NO. 3-OgLucL27V
ATGGTGTTTACACTCGAAGATTTCGTAGGGGACTGGCGGCAGACAGCCGGCTACAACCTGGACCAAGT
CCTTGAGCAGGGCGGTGTGTCCAGTTTGTTTCAGAATCTCGGGGTGTCCGTAACTCCGATCCAAAGGA
TTGTCCTGAGCGGTGAAAACGGCCTGAAGATCGACATCCATGTCATCATCCCGTATGAAGGTCTGAGC

| SEQUENCES |
|---|
| GGCGATCAGATGGGCCAGATCGAAAAAATTTTTAAGGTGGTGTACCCTGTGGATGATCATCACTTTAA<br>GGTGATTCTGCACTATGGCACACTGGTAATCGACGGGGTTACGCCGAACATGATCGACTATTTCGGAC<br>GGCCGTATGAAGGGCATCGCCGTGTTCGACGGCAAAAAGATCACTGTAACCGGGACCCTGTGGAACGGC<br>AACAAAATTATCGACGAGCGCCTGATCAACCCCGACGGCTCCCTGCTGTTCCGCGTAACCATCAACGG<br>AGTGACCGGCTGGCGGCTGTGCGAGCGCATTTTGGCG |
| SEQ ID NO. 4-UltraGlo FFluc<br>GCTGACAAAACATCCTGTATGGTCCGGAACCGTTCTACCCACTGGAAGATGGTACCGCTGGTGAACA<br>GATGTTTGACGCATTATCTCGTTATGCAGCTATTCCGGGCTGCATAGCATTGACAAATGCTCATACAA<br>AAGAAAATGTTTTATATGAAGAGTTTCTGAAACTGTCGTGTCGTTTAGCGGAAAGTTTTAAAAAGTAT<br>GGATTAAAACAAAACGACACAATAGCGGTGTGTAGCGAAAATAGTCTGCAATTTTTCCTTCCTGTAAT<br>TGCATCATTGTATCTTGGAATAATTGTGGCACCTGTTAACGATAAATACATTGAACGTGAATTAATAC<br>ACAGTCTTGGTATTGTAAAACCACGCATAGTTTTTTGCTCCAAGAATACTTTTCAAAAGTACTGAAT<br>GTAAAATCTAAATTAAAATCTATTGAAACTATTATTATATTAGACTTAAATGAAGACTTAGGAGGTTA<br>TCAATGCCTCAACAACTTTATTTCTCAAAATTCCGATAGTAATCTGGACGTAAAAAAATTTAAACCCT<br>ATTCTTTAATCGAGACGATCAGGTTGCGTCGATTATGTTTTCTTCTGGTACAACTGGTCTGCCGAAG<br>GGAGTCATGCTAACTCACAAGAATATTGTTGCACGATTTTCTATTGCAAAAGATCCTACTTTTGGTAA<br>CGCAATTAATCCCACGTCAGCAATTTTAACGGTAATACCTTTCCACCATGGTTTTGGTATGATGACCA<br>CATTAGGATACTTTACTTGTGGATTCCGAGTTGTTCTAATGCACACGTTTGAAGAAAACTATTTCTA<br>CAATCATTACAAGATTATAAAGTGGAAAGTACTTTACTTGTACCAACATTAATGGCATTTCTTGCAAA<br>AAGTGCATTAGTTGAAAAGTACGATTTATCGCACTTAAAAGAAATTGCATCTGGTGGCGCACCTTTAT<br>CAAAAGAAATTGGGGAGATGGTGAAAAAACGGTTTAAATTAAACTTTGTCAGGCAAGGGTATGGATTA<br>ACAGAAACCACTTCGGCTGTTTTAATTACACCGAAAGGTGACGCCAAACCGGGATCAACTGGTAAAAT<br>AGTACCATTACACGCTGTTAAAGTTGTCGATCCTACAACAGGGAAAATTTTGGGGCCAAATGAACCTG<br>GAGAATTGTATTTTAAAGGCCCGATGATAATGAAGGGGTTATTATAATAATGAAGAAGCTACTAAAGCA<br>ATTATTGATAATGACGGATGGTTGCGCTCTGGTGATATTGCTTATTATGACAATGATGGCCATTTTTA<br>TATTGTGGACAGGCTGAAGTCACTGATTAAATATAAAGGTTATCAGGTTGCACCTGCTGAAATTGAGG<br>GAATACTCTTACAACATCCGTATATTGTTGATGCCGGCGTTACTGGTATACCGGATGAAGCCGCGGGC<br>GAGCTTCCAGCTGCAGGTGTTGTAGTACAGACTGGAAAATATCTAAACGAACAAATCGTACAAGATTA<br>TGTTGCCAGTCAAGTTTCAACAGCCAAATGGCTACGTGGTGGGGTGAAATTTTTGGATGAAATTCCCA<br>AAGGATCAACTGGAAAAATTGACAGAAAAGTGTTAAGACAAATGTTAGAAAAAACACACCAATGGG |
| SEQ ID NO. 5-AT1R<br>ATGATTCTCAACTCTTCTACTGAAGATGGTATTAAAAGAATCCAAGATGATTGTCCCAAAGCTGGAAG<br>GCATAATTACATATTTGTCATGATTCCTACTTTATACAGTATCATCTTTGTGGTGGGAATATTTGGAA<br>ACAGCTTGGTGGTGATAGTCATTTACTTTTATATGAAGCTGAAGCTGTGGCCAGTGTTTTCTTTTG<br>AATTTAGCACTGGCTGACTTATGCTTTTTACTGACTTTGCCACTATGGGCTGTCTACACAGCTATGGA<br>ATACCGCTGGCCCTTTGGCAATTACCTATGTAAGATTGCTTCAGCCAGCGTCAGTTTCAACCTGTACG<br>CTAGTGTGTTTCTACTCACGTGTCTCAGCATTGATCGATACCTGGCTATTGTTCACCCAATGAAGTCC<br>CGCCTTCGACGCACAATGCTTGTAGCCAAAGTCACCTGCATCATCATTTGGCTGCTGGCAGGCTTGGC<br>CAGTTTGCCAGCTATAATCCATCGAAATGTATTTTTCATTGAGAACACCAATATTACAGTTTGTGCTT<br>TCCATTATGAGTCCCAAAATTCAACCCTTCCGATAGGGCTGGGCCTGACCAAAAATATACTGGGTTTC<br>CTGTTTCCTTTTCTGATCATTCTTACAAGTTATACTCTTATTTGGAAGGCCCTAAAGAAGGCTTATGA<br>AATTCAGAAGAACAAACCAAGAAATGATGATATTTTAAGATAATTATGGCAATTGTGCTTTTCTTTT<br>TCTTTTCCTGGATTCCCCACCAAATATTCACTTTTCTGGATGTATTGATTCAACTAGGCATCATACGT<br>GACTGTAGAATTGCAGATATTGTGGACACGGCCATGCCTATCACCATTTGTATAGCTTATTTTAACAA<br>TTGCCTGAATCCTCTTTTTTATGGCTTTCTGGGGAAAAAAATTTAAAAGATATTTTCTCCAGCTTCTAA<br>AATATATTCCCCCAAAAGCCAAATCCCACTCAAACCTTTCAACAAAAATGAGCACGCTTTCCTACCGC<br>CCCTCAGATAATGTAAGCTCATCCACCAAGAAGCCTGCACCATGTTTTGAGGTTGAGTGA |
| SEQ ID NO. 6-OPRD1<br>ATGGAACCGGCCCCCTCCGCCGGCGCCGAGCTGCAGCCCCCGCTCTTCGCCAACGCCTCGGACGCCTA<br>CCCTAGCGCCTGCCCCAGCGCTGGCGCCAATGCGTCGGGGCCGCCAGGCGCGCGGAGCGCCTCGTCCC<br>TCGCCCTGGCAATCGCCATCACCGCGCTCTACTCGGCCGTGTGCGCCGTGGGCGTGCTGGGCAACGTG<br>CTTGTCATGTTCGGCATCGTCCGGTACACTAAGATGAAGACGGCCACCAACATCTACATCTTCAACCT<br>GGCCTTAGCCGATGCGCTGGCCACCAGCACGCGCTGCCTTTCCAGAGTGCCAAGTACCTGATGGAGACGT<br>GGCCCTTCGGCGAGCTGCTCTGCAAGGCTGTGCTCTCCATCGACTACTACAATATGTTCACCAGCATC<br>TTCACGCTCACCATGATGAGTGTTGACCGCTACATCGCTGTCTGCCACCCTGTCAAGGCCCTGGACTT<br>CCGCACGCCTGCCAAGGCCAAGCTGATCAACATCTGTATCTGGGTCCTGGCCTCAGGCGTTGGCGTGC<br>CCATCATGGTCATGGCTGTGACCCGTCCCCGGGACGGGGCAGTGGTGTGCATGCTCCAGTTCCCCAGC<br>CCCAGCTGGTACTGGGACACGGTGACCAAGATCTGCGTGTTCCTCTTCGCCTTCGTGGTGCCCATCCT<br>CATCATCACCGTGTGCTATGGCCTCATGCTGCTGCGCCTGCGCAGTGTGCGCCTGCTGTCGGGCTCCA<br>AGGAGAAGGACCGCAGCCTGCGGCGCATCACGCGCATGGTGCTGGTGGTTGTGGGCGCCTTCGTGGTG<br>TGTTGGGCGCCCATCCACATCTTCGTCATCGTCTGGACGCTGGTGGACATCGACCGGCGCGACCCGCT<br>GGTGGTGGCTGCGCTGCACCTGTGCATCGCGCTGGGTTACGCCAATAGCAGCCTCAACCCCGTGCTCT<br>ACGCTTTCCTCGACGAGAACTTCAAGCGCTGCTTCCGCCAGCTCTGCCGCAAGCCCTGCGGCCGCCCA<br>GACCCCAGCAGCTTCAGCCGCGCGCCCGCGAAGCCACGGCCCGCGAGCGTGTCACCGCCTGCACCCCGTC<br>CGATGGTCCCGGCGGTGGCGCTGCCGCCTGA |
| EQ ID NO. 7-EGFR<br>CTGGAGGAAAAGAAAGTTTGCCAAGGCACGAGTAACAAGCTCACGCAGTTGGGCACTTTTGAAGATCA<br>TTTTCTCAGCCTCCAGAGGATGTTCAATAACTGTGAGGTGGTCCTTGGGAATTTGGAAATTACCTATG<br>TGCAGAGGAATTATGATCTTTCCTTCTTAAAGACCATCCAGGAGGTGGCTGGTTATGTCCTCATTGCC<br>CTCAACACAGTGGAGCGAATTCCTTTGGAAAACCTGCAGATCATCAGAGGAAATATGTACTACGAAAA<br>TTCCTATGCCTTAGCAGTCTTATCTAACTATGATGCAAATAAAACCGGACTGAAGGAGCTGCCCATGA<br>GAAATTTACAGGAAATCCTGCATGGCGCCGTGCGGTTCAGCAACAACCCTGCCCTGTGCAACGTGGAG<br>AGCATCCAGTGGCGGGACATAGTCAGCAGTGACTTTCTCAGCAACATGTCGATGGACTTCCAGAACCA |

| SEQUENCES |
|---|
| CCTGGGCAGCTGCCAAAAGTGTGATCCAAGCTGTCCCAATGGGAGCTGCTGGGGTGCAGGAGAGGAGA
ACTGCCAGAAACTGACCAAAATCATCTGTGCCCAGCAGTGCTCCGGGCGCTGCCGTGGCAAGTCCCCC
AGTGACTGCTGCCACAACCAGTGTGCTGCAGGCTGCACAGGCCCCGGGAGAGCGACTGCCTGGTCTG
CCGCAAATTCCGAGACGAAGCCACGTGCAAGGACACCTGCCCCCCACTCATGCTCTACAACCCCACCA
CGTACCAGATGGATGTGAACCCCGAGGGCAAATACAGCTTTGGTGCCACCTGCGTGAAGAAGTGTCCC
CGTAATTATGTGGTGACAGATCACGGCTCGTGCGTCCGAGCCTGTGGGGCCGACAGCTATGAGATGGA
GGAAGACGGCGTCCGCAAGTGTAAGAAGTGCAAGGGCCTTGCCGCAAAGTGTGTAACGGAATAGGTA
TTGGTGAATTTAAAGACTCACTCTCCATAAATGCTACGAATATTAAACACTTCAAAAACTGCACCTCC
ATCAGTGGCGATCTCCACATCCTGCCGGTGGCATTTAGGGGTGACTCCTTCACACATACTCCTCCTCT
GGATCCACAGGAACTGGATATTCTGAAAACCGTAAAGGAAATCACAGGGTTTTTGCTGATTCAGGCTT
GGCCTGAAAACAGGACGGACCTCCATGCCTTTGAGAACCTAGAAATCATACGCGGCAGGACCAAGCAA
CATGGTCAGTTTTCTCTTGCAGTCGTCAGCCTGAACATAACATCCTTGGGATTACGCTCCCTCAAGGA
GATAAGTGATGGAGATGTGATAATTTCAGGAAACAAAAATTTGTGCTATGCAAATACAATAAACTGGA
AAAAACTGTTTGGGACCTCCGGTCAGAAAACCAAATTATAAGCAACAGAGGTGAAAACAGCTGCAAG
GCCACAGGCCAGGTCTGCCATGCCTTGTGCTCCCCCGAGGGCTGCTGGGGCCCGGAGCCCAAGGACTG
CGTCTCTTGCCGGAATGTCAGCCGAGGCAGGGAATGCGTGGACAAGTGCAACCTTCTGGAGGGTGAGC
CAAGGGAGTTTGTGGAGAACTCTGAGTGCATACAGTGCCACCCAGAGTGCCTGCCTCAGGCCATGAAC
ATCACCTGCACAGGACGGGACCAGACAACTGTATCCAGTGTGCCCACTACATTGACGGCCCCCACTG
CGTCAAGACCTGCCCGGCAGGAGTCATGGGAGAAAACAACACCCTGGTCTGGAAGTACGCAGACGCCG
GCCATGTGTGCCACCTGTGCCATCCAAACTGCACCTACGGATGCACAGGGCCAGGTCTTGAAGGCTGT
CCAACGAATGGGCCTAAGATCCCGTCCATCGCCACTGGGATGGTGGGGCCCTCCTCTTGCTGCTGGT
GGTGGCCCTGGGGATCGGCCTCTTCATGCGAAGGCGCCACATCGTTCGGAAGCGCACGCTGCGGAGGC
TGCTGCAGGAGAGGGAGCTTGTGGAGCCTCTTACACCCAGTGGAGAAGCTCCCAACCAAGCTCTCTTG
AGGATCTTGAAGGAAACTGAATTCAAAAAGATCAAAGTGCTGGGCTCCGGTGCGTTCGGCACGGTGTA
TAAGGGACTCTGGATCCCAGAAGGTGAGAAAGTTAAAATTCCCGTCGCTATCAAGGAATTAAGAGAAG
CAACATCTCCGAAAGCCAACAAGGAAATCCTCGATGAAGCCTACGTGATGGCCAGCGTGGACAACCCC
CACGTGTGCCGCCTGCTGGGCATCTGCCTCACCTCCACCGTGCAGCTCATCACGCAGCTCATGCCCTT
CGGCTGCCTCCTGGACTATGTCCGGGAACACAAAGACAATATTGGCTCCCAGTACCTGCTCAACTGGT
GTGTGCAGATCGCAAAGGGCATGAACTACTTGGAGGACCGTCGCTTGGTGCACCGCGACCTGGCAGCC
AGGAACGTACTGGTGAAAACACCGCAGCATGTCAAGATCACAGATTTTGGGCTGGCCAAACTGCTGGG
TGCGGAAGAGAAAGAATACCATGCAGAAGGAGGCAAAGTGCCTATCAAGTGGATGGCATTGGAATCAA
TTTTACACAGAATCTATACCCACCAGATGATGTCTGGAGCTACGGGGTGACCGTTTGGGAGTTGATG
ACCTTTGGATCCAAGCCATATGACGGAATCCCTGCCAGCGAGATCTCCTCCATCCTGGAGAAAGGAGA
ACGCCTCCCTCAGCCACCCATATGTACCATCGATGTCTACATGATCATGGTCAAGTGCTGGATGATAG
ACGCAGATAGTCGCCCAAAGTTCCGTGAGTTGATCATCGAATTCTCCAAAATGGCCCGAGACCCCCAG
CGCTACCTTGTCATTCAGGGGGATGAAAGAATGCATTTGCCAAGTCCTACAGACTCCAACTTCTACCG
TGCCCTGATGGATGAAGAAGACATGGACGACGTGGTGGATGCCGACGAGTACCTCATCCCACAGCAGG
GCTTCTTCAGCAGCCCCTCCACGTCACGGACTCCCCTCCTGAGCTCTCTGAGTGCAACCAGCAACAAT
TCCACCGTGGCTTGCATTGATAGAAATGGGCTGCAAAGCTGTCCCATCAAGGAAGACAGCTTCTTGCA
GCGATACAGCTCAGACCCCACAGGCGCCTTGACTGAGGACAGCATAGACGACACCTTCCTCCCAGTGC
CTGAATACATAAACCAGTCCGTTCCCAAAAGGCCCGCTGGCTCTGTGCAGAATCCTGTCTATCACAAT
CAGCCTCTGAACCCCGCGCCCAGCAGAGACCCACACTACCAGGACCCCCACAGCACTGCAGTGGGCAA
CCCCGAGTATCTCAACACTGTCCAGCCCACCTGTGTCAACAGCACATTCGACAGCCCTGCCCACTGGG
CCCAGAAAGGCAGCCACCAAATTAGCCTGGACAACCCTGACTACCAGCAGGACTTCTTTCCCAAGGAA
GCCAAGCCAAATGGCATCTTTAAGGGCTCCACAGCTGAAAATGCAGAATACCTAAGGGTCGCGCCACA
AAGCAGTGAATTTATTGGAGCAGTTTAA |

SEQ ID NO. 8-EDG1
ATGGGGCCCACCAGCGTCCCGCTGGTCAAGGCCCACCGCAGCTCGGTCTCTGACTACGTCAACTATGA
TATCATCGTCCGGCATTACAACTACACGGGAAAGCTGAATATCAGCGCGGACAAGGAGAACAGCATTA
AACTGACCTCGGTGGTGTTCATTCTCATCTGCTGCTTTATCATCCTGGAGAACATCTTTGTCTTGCTG
ACCATTTGGAAAACCAAGAAATTCCACCGACCCATGTACTATTTTATTGGCAATCTGGCCCTCTCAGA
CCTGTTGGCAGGAGTAGCCTACACAGCTAACCTGCTCTTGTCTGGAGCCACCACCTACAAGCTCACTC
CCGCCCAGTGGTTTCTGCGGGAAGGGAGTATGTTTGTGGCCCTGTCAGCCTCCGTGTTCAGTCTCCTC
GCCATCGCCATTGAGCGCTATATCACAATGCTGAAAATGAAACTCCACAACGGGAGCAATAACTTCCG
CCTCTTCCTGCTAATCAGCGCCTGCTGGGTCATCTCCCTCATCCTGGGTGGCCTGCCTATCATGGGCT
GGAACTGCATCAGCGCGCTGTCCAGCTGCTCCACCGTGCTGCCGCTCTACCACAAGCACTATATCCTC
TTCTGCACCACCGTCTTCACTCTGCTTCTGCTCTCCATCGTCATTCTGTACTGCAGAATCTACTCCTT
GGTCAGGACTCGGAGCCGCCGCCTGACGTTCCGCAAGAACATTTCCAAGGCCAGCCGCAGCTCTGAGA
AGTCGCTGGCGCTGCTCAAGACCGTAATTATCGTCCTGAGCGTCTTCATCGCCTGCTGGGCACCGCTC
TTCATCCTGCTCCTGCTGGATGTGGGCTGCAAGGTGAAGACCTGTGACATCCTCTTCAGAGCGGAGTA
CTTCCTGGTGTTAGCTGTGCTCAACTCCGGCACCAACCCCATCATTTACACTCTGACCAACAAGGAGA
TGCGTCGGGCCTTCATCCGGATCATGTCCTGCTGCAAGTGCCCGAGCGGAGACTCTGCTGGCAAATTC
AAGCGACCCATCATCGCCGGCATGGAATTCAGCCGCAGCAAATCGGACAATTCCTCCCACCCCCAGAA
AGACGAAGGGGACAACCCAGAGACCATTATGTCTTCTGGAAACGTCAACTCTTCTTCCTAG

SEQ ID NO. 9-AVPR2
CTCATGGCGTCCACCACTTCCGCTGTGCCTGGGCATCCCTCTCTGCCCAGCCTGCCCAGCAACAGCAG
CCAGGAGAGGCCACTGGACACCCGGGACCCGCTGCTAGCCCGGGCGGAGCTGGCGCTGCTCTCCATAG
TCTTTGTGGCTGTGGCCCTGAGCAATGGCCTGGTGCTGGCGGCCCTAGCTCGGCGGGGCCGGCGGGGC
CACTGGGCACCCATACACGTCTTCATTGGCCACTTGTGCCTGGCCGACCTGGCCGTGGCTCTGTTCCA
AGTGCTGCCCCAGCTGGCCTGGAAGGCCACCGACCGCTTCCGTGGGCCAGATGCCCTGTGTCGGGCCG
TGAAGTATCTGCAGATGGTGGGCATGTATGCCTCCTCCTACATGATCCTGGCCATGACGCTGGACCGC
CACCGTGCCATCTGCCGTCCCATGCTGGCGTACCGCCATGGAAGTGGGGCTCACTGGAACCGGCCGGT
GCTAGTGGCTTGGGCCTTCTCGCTCCTTCTCAGCCTGCCCCAGCTCTTCATCTTCGCCCAGCGCAACG
TGGAAGGTGGCAGCGGGGTCACTGACTGCTGGGCCTGCTTTGCGGAGCCCTGGGGCCGTCGCACCTAT
GTCACCTGGATTGCCCTGATGGTGTTCGTGGCACCTACCCTGGGTATCGCCGCCTGCCAGGTGCTCAT

| SEQUENCES |
|---|
| CTTCCGGGAGATTCATGCCAGTCTGGTGCCAGGGCCATCAGAGAGGCCTGGGGGCGCCGCAGGGGAC
GCCGGACAGGCAGCCCCGGTGAGGGAGCCCACGTGTCAGCAGCTGTGGCCAAGACTGTGAGGATGACG
CTAGTGATTGTGGTCGTCTATGTGCTGTGCTGGGCACCCTTCTTCCTGGTGCAGCTGTGGGCCGCGTG
GGACCCGGAGGCACCTCTGGAAGGGGCGCCCTTTGTGCTACTCATGTTGCTGGCCAGCCTCAACAGCT
GCACCAACCCCTGGATCTATGCATCTTTCAGCAGCAGCGTGTCCTCAGAGCTGCGAAGCTTGCTCTGC
TGTGCCCGGGGACGCACCCCACCCAGCCTGGGTCCCCAAGATGAGTCCTGCACCACCGCCAGCTCCTC
CCTGGCCAAGGACACTTCATCG

SEQ ID NO. 10-ADRB2
GGGCAACCCGGGAACGGCAGCGCCTTCTTGCTGGCACCCAATAGAAGCCATGCGCCGGACCACGACGT
CACGCAGCAAAGGGACGAGGTGTGGGTGGTGGGCATGGGCATCGTCATGTCTCTCATCGTCCTGGCCA
TCGTGTTTGGCAATGTGCTGGTCATCACAGCCATTGCCAAGTTCGAGCGTCTGCAGACGGTCACCAAC
TACTTCATCACTTCACTGGCCTGTGCTGATCGGTCATGGGCCTGGCAGTGGTGCCCTTTGGGGCCGC
CCATATTCTTATGAAAATGTGGACTTTTGGCAACTTCTGGTGCGAGTTTTGGACTTCCATTGATGTGC
TGTGCGTCACGGCCAGCATTGAGACCCTGTGCGTGATCGCGGTGGATCGCTACTTTGCCATTACTTCA
CCTTTCAAGTACCAGAGCCTGCTGACCAAGAATAAGGCCCGGGTGATCATTCTGATGGTGTGGATTGT
GTCAGGCCTTACCTCCTTCTTGCCCATTCAGATGCACTGGTACCGGGCCACCCACCAGGAAGCCATCA
ACTGCTATGCCAATGAGACCTGCTGTGACTTCTTCACGAACCAAGCCTATGCCATTGCCTCTTCCATC
GTGTCCTTCTACGTTCCCCTGGTGATCATGGTCTTCGTCTACTCCAGGGTCTTTCAGGAGGCCAAAAG
GCAGCTCCAGAAGATTGACAAATCTGAGGGCCGCTTCCATGTCCAGAACCTTAGCCAGGTGGAGCAGG
ATGGGCGGACGGGGCATGGACTCCGCAGATCTTCCAAGTTCTGCTTGAAGGAGCACAAAGCCCTCAAG
ACGTTAGGCATCATCATGGGCACTTTCACCCTCTGCTGGCTGCCCTTCTTCATCGTTAACATTGTGCA
TGTGATCCAGGATAACCTCATCCGTAAGGAAGTTTACATCCTCCTAAATTGGATAGGCTATGTCAATT
CTGGTTTCAATCCCCTTATCTACTGCCGGAGCCCAGATTTCAGGATTGCCTTCCAGGAGCTTCTGTGC
CTGCGCAGGTCTTCTTTGAAGGCCTATGGGAATGGCTACTCCAGCAACGGCAACAGGGGAGCAGAG
TGGATATCACGTGGAACAGGAGAAAGAAAATAAACTGCTGTGTGAAGACCTCCCAGGCACGGAAGACT
TTGTGGGCCATCAAGGTACTGTGCCTAGCGATAACATTGATTCACAAGGGAGGAATTGTAGTACAAAT
GACTCACTGCTGTAA

SEQ ID NO. 11-luc2 FFluc
GCCAAAAACATTAAGAAGGGCCCAGCGCCATTCTACCCACTCGAAGACGGGACCGCCGGCGAGCAGCT
GCACAAAGCCATGAAGCGCTACGCCCTGGTGCCCGGCACCATCGCCTTTACCGACGCACATATCGAGG
TGGACATTACCTACGCCGAGTACTTCGAGATGAGCGTTCGGCTGGCAGAAGCTATGAAGCGCTATGGG
CTGAATACAAACCATCGGATCGTGGTGTGCAGCGAGAATAGCTTGCAGTTCTTCATGCCCGTGTTGGG
TGCCCTGTTCATCGGTGTGGCTGTGGCCCCAGCTAACGACATCTACAACGAGCGCGAGCTGCTGAACA
GCATGGGCATCAGCCAGCCCACCGTCGTATTCGTGAGCAAGAAAGGGCTGCAAAAGATCCTCAACGTG
CAAAAGAAGCTACCGATCATACAAAAGATCATCATCATGGATAGCAAGACCGACTACCAGGGCTTCCA
AAGCATGTACACCTTCGTGACTTCCCATTTGCCACCCGGCTTCAACGAGTACGACTTCGTGCCCGAGA
GCTTCGACCGGGACAAAACCATCGCCCTGATCATGAACAGTAGTGGCAGTACCGGATTGCCCAAGGGC
GTAGCCCTACCGCACCGCACCGCTTGTGTCCGATTCAGTCATGCCGCGACCCCATCTTCGGCAACCA
GATCATCCCCGACACCGCTATCCTCAGCGTGGTGCCATTTCACCACGGCTTCGGCATGTTCACCACGC
TGGGCTACTTGATCTGCGGCTTTCGGGTCGTGCTCATGTACCGCTTCGAGGAGGAGCTATTCTTGCGC
AGCTTGCAAGACTATAAGATTCAATCTGCCCTGCTGGTGCCCACACTATTTAGCTTCTTCGCTAAGAG
CACTCTCATCGACAAGTACGACCTAAGCAACTTGCACGAGATCGCCAGCGGCGGGGCGCCGCTCAGCA
AGGAGGTAGGTGAGGCCGTGGCCAAACGCTTCCACCTACCAGGCATCCGCCAGGGCTACGGCCTGACA
GAAACAACCAGCGCCATTCTGATCACCCCCGAAGGGGACGACAAGCCTGGCGCAGTAGGCAAGGTGGT
GCCCTTCTTCGAGGCTAAGGTGGTGGACTTGGACACCGGTAAGACACTGGGTGTGAACCAGCGCGGCG
AGCTGTGCGTCCGTGGCCCCATGATCATGAGCGGCTACGTTAACAACCCCGAGGCTACAAACGCTCTC
ATCGACAAGGACGGCTGGCTGCACAGCGGCGACATCGCCTACTGGGACGAGGACGAGCACTTCTTCAT
CGTGGACCGGCTGAAGAGCCTGATCAAATACAAGGGCTACCAGGTAGCCCCAGCCGAACTGGAGAGCA
TCCTGCTGCAACACCCCAACATCTTCGACGCCGGGGTCGCCGGCCTGCCCGACGACGATGCCGGCGAG
CTGCCCGCCGCAGTCGTCGTGCTGGAACACGGTAAAACCATGACCGAGAAGGAGATCGTGGACTATGT
GGCCAGCCAGGTTACAACCGCCAAGAAGCTGCGCGGTGGTGTTGTGTTCGTGGACGAGGTGCCTAAAG
GACTGACCGGCAAGTTGGACGCCCGCAAGATCCGCGAGATTCTCATTAAGGCCAAGAAG SEQ ID NO: 12-OgLuc 9B8
ATGGTGTTTACATTGGAGGATTTCGTTGGAGACTGGCGGCAGACAGCTGGATACAACCAAGATCAAGT
GTTAGAACAAGGAGGATTGTCTAGTCTGTTCCAAAAGCTGGGAGTGTCAGTCACCCCAATCCAGAAAA
TTGTGCTGTCTGGGGAGAATGGGTTAAAAATTGATATTCATGTCATCATCCCTTACGAGGGACTCAGT
GGTTTTCAAATGGGTCTGATTGAAATGATCTTCAAAGTTGTTTACCCAGTGGATGATCATCATTTCAA
GGTTATTCTCCATTATGGTACACTCGTTATTGACGGTGTGACACCAAACATGATTGACTACTTTGGAC
GCCCTTACGAGGGAATTGCTGTGTTTGACGGCAAGAAGATCACAGTTACTGGAACTCTGTGGAACGGC
AACAAGATCATTGATGAGCGCCTGATCAACCCAGATGGTTCACTCCTCTTCCGCGTTACTATCAATGG
AGTCACCGGATGGCGCCTTTGCGAGCGTATTCTTGCC |

We claim:

1. A method of detecting endocytosis comprising:
   a) expressing a fusion protein in a cell comprising a cell membrane, wherein said fusion protein comprises a cell-surface receptor protein and a reporter protein, and said expressing results in the co-expression of the cell surface receptor protein and the reporter protein as a single fusion protein in the cell, wherein the reporter protein is displayed extracellularly when the cell-surface receptor is incorporated into the cell membrane of the cell;
   b) delivering a reporter substrate to the cell, wherein an association between the reporter protein and reporter substrate produces a detectable signal when the association occurs extracellularly and an altered signal when the association occurs intracellularly; and
   c) monitoring said detectable signal and said altered signal, wherein a transition from said detectable signal to said altered signal indicates endocytosis of the fusion protein.

2. The method of detecting endocytosis of claim 1, wherein monitoring of said detectable signal comprises:
   i) inducing endocytosis of said fusion protein; and
   ii) detecting said detectable signal and said altered signal after inducing endocytosis.

3. The method of detecting endocytosis of claim 1, wherein monitoring of said detectable signal comprises:
   i) detecting said signal prior to endocytosis;
   ii) allowing endocytosis of said fusion protein;
   iii) detecting said signal following endocytosis; and
   iv) comparing said signal from step (i) to said signal from step (iii) to detect endocytosis.

4. The method of claim 1, wherein said reporter protein comprises a luciferase enzyme.

5. The method of claim 4, wherein the luciferase enzyme is a beetle or *Oplophorus* luciferase enzyme or a mutant or variant thereof.

6. The method of claim 1, wherein endocytosis results in movement of said reporter protein from an extracellular space into an endosome.

7. The method of claim 6, wherein said signal is detectably altered within said endosome compared to the extracellular space.

8. The method of claim 6, wherein said signal is reduced within said endosome compared to the extracellular space.

9. The method of claim 1, wherein said reporter substrate is a luciferin, luciferin derivative, coelenterazine or coelenterazine derivative.

10. The method of claim 3, further comprising a step between steps (i) and (ii) of triggering endocytosis.

* * * * *